US009370324B2

(12) United States Patent
Barrett et al.

(10) Patent No.: US 9,370,324 B2
(45) Date of Patent: Jun. 21, 2016

(54) HEMODIALYSIS PATIENT DATA ACQUISITION, MANAGEMENT AND ANALYSIS SYSTEM

(75) Inventors: Louis LeeGrande Barrett, West Point, UT (US); David Wayne Peterson, Clinton, UT (US); Brian Harris Nathanson, Longmeadow, MA (US); Michael Jack Germain, Hampden, MA (US); Michael K. Black, Layton, UT (US)

(73) Assignee: FRESENIUS MEDICAL CARE HOLDINGS, INC., Waltham, MA (US)

( * ) Notice: Subject to any disclaimer, the term of this patent is extended or adjusted under 35 U.S.C. 154(b) by 736 days.

(21) Appl. No.: 12/265,386

(22) Filed: Nov. 5, 2008

(65) Prior Publication Data

US 2010/0113891 A1 May 6, 2010

(51) Int. Cl.
| | |
|---|---|
| *G01N 33/48* | (2006.01) |
| *A61B 5/145* | (2006.01) |
| *A61B 5/1455* | (2006.01) |
| *A61M 1/16* | (2006.01) |
| *G06F 19/00* | (2011.01) |
| *G06Q 50/24* | (2012.01) |
| *A61M 1/36* | (2006.01) |
| *G06G 7/58* | (2006.01) |

(52) U.S. Cl.
CPC ......... *A61B 5/14535* (2013.01); *A61B 5/14557* (2013.01); *A61M 1/16* (2013.01); *A61M 1/361* (2014.02); *G06F 19/322* (2013.01); *G06F 19/3406* (2013.01); *G06F 19/3481* (2013.01); *G06Q 50/24* (2013.01); *A61B 2562/08* (2013.01); *A61M 2205/3313* (2013.01); *A61M 2205/3553* (2013.01); *A61M 2205/3592* (2013.01); *A61M 2205/52* (2013.01)

(58) Field of Classification Search
CPC .................. G06F 19/3481; G06F 19/3406
USPC .......... 604/403, 408, 411, 412, 414, 415, 416
See application file for complete search history.

(56) References Cited

U.S. PATENT DOCUMENTS

| | | | |
|---|---|---|---|
| 2,357,238 | A | 8/1944 | Trimble |
| D206,714 | S | 1/1967 | Badkar |
| D212,218 | S | 9/1968 | Norton |
| 3,507,951 | A | 4/1970 | Baily |
| 3,580,683 | A | 5/1971 | Schulkind |
| 3,728,032 | A | 4/1973 | Noll |
| 3,740,156 | A | 6/1973 | Heigl et al. |
| 4,243,883 | A | 1/1981 | Schwarzmann |
| D270,281 | S | 8/1983 | Andersen et al. |
| 4,444,498 | A | 4/1984 | Heinemann |
| 4,784,768 | A | 11/1988 | Mathieu |
| 4,936,993 | A | 6/1990 | Nomura |
| 5,073,171 | A | 12/1991 | Eaton |
| 5,171,456 | A | 12/1992 | Hwang et al. |
| D335,096 | S | 4/1993 | Marsch |
| 5,222,948 | A | 6/1993 | Austin et al. |
| 5,231,464 | A | 7/1993 | Ichimura et al. |
| 5,247,434 | A | 9/1993 | Peterson et al. |
| 5,312,535 | A | 5/1994 | Waska et al. |
| 5,351,686 | A | 10/1994 | Steuer et al. |
| 5,366,630 | A | 11/1994 | Chevallet |
| 5,372,136 | A | 12/1994 | Steuer et al. |
| 5,456,253 | A | 10/1995 | Steuer et al. |
| 5,458,566 | A | 10/1995 | Herrig et al. |
| 5,476,764 | A | 12/1995 | Bitensky |

(Continued)

FOREIGN PATENT DOCUMENTS

| | | |
|---|---|---|
| CN | 101015455 A | 8/2007 |
| CN | 101113477 A | 1/2008 |

(Continued)

OTHER PUBLICATIONS

Steuer et al., "Optical Measurement of Hematocrit and Other Biological Constituents in Renal Therapy", Advances in Renal Replacement Therapy, vol. 6, No. 3 Jul. 1999, pp. 217-224.
Gardner, "Exponential Smoothing: The State of the Art", Journal of Forecasting, vol. 4, 1985, pp. 1-28.
Baum, "An Introduction to Modern Econometrics Using Strata", StrataCorp. LP, 2006, Chapter 9, pp. 219-245.
Office action for co-pending Canadian Patent Application No. 2,742,619, dated Aug. 5, 2013.

(Continued)

*Primary Examiner* — Eric S Dejong
(74) *Attorney, Agent, or Firm* — Leydig, Voit & Mayer, Ltd.

(57) ABSTRACT

A hemodialysis patient data acquisition and management system resides on a host computer which receives information from one or more non-invasive, optical blood monitors associated with a hemodialysis system. When a patient is undergoing hemodialysis treatment, a sensor assembly monitors the patient's blood flowing through the hemodialysis system and a controller for the blood monitor generates data which includes at least an identification code for the patient undergoing the treatment on the respective system, and non-invasively determined blood data taken at the onset of the scheduled treatment, such as initial Hgb, HCT, and SAT values. A host computer communicates with the one or more optical blood monitors, preferably via a wireless network, and the patient's session commencement data is downloaded to the host computer. The host computer includes a patient database containing historical session commencement data for a plurality of patients, as well as screen displays for displaying historical data for individual patients, such as Hgb trends. The system also preferably provides a predictive algorithm for the patient's Hgb at the patient's next scheduled hemodialysis treatment session. The preferred system also includes software that provides a recommended dose of the anemia management drug for the patient.

7 Claims, 12 Drawing Sheets

(56) References Cited

U.S. PATENT DOCUMENTS

| | | |
|---|---|---|
| 5,531,686 A | 7/1996 | Lundquist et al. |
| 5,670,050 A | 9/1997 | Brose et al. |
| 5,674,390 A | 10/1997 | Matthews et al. |
| 5,676,644 A | 10/1997 | Toavs et al. |
| 5,729,333 A | 3/1998 | Osten et al. |
| 5,730,712 A | 3/1998 | Falkvall et al. |
| 5,762,805 A | 6/1998 | Truitt et al. |
| 5,769,815 A | 6/1998 | Utterberg |
| 5,779,529 A | 7/1998 | Bizer |
| 5,792,052 A | 8/1998 | Isaacson et al. |
| D409,750 S | 5/1999 | Hacker |
| 6,018,673 A | 1/2000 | Chin et al. |
| 6,069,687 A | 5/2000 | Briggs |
| 6,090,061 A | 7/2000 | Steuer et al. |
| 6,284,131 B1 | 9/2001 | Hogard et al. |
| 6,284,142 B1 | 9/2001 | Muller |
| 6,510,330 B1 | 1/2003 | Enejder |
| 6,554,788 B1 | 4/2003 | Hunley et al. |
| 6,746,415 B1 | 6/2004 | Steuer et al. |
| 6,784,820 B1 | 8/2004 | Casalegno et al. |
| 7,018,353 B2 | 3/2006 | Hunley et al. |
| D518,573 S | 4/2006 | French |
| 7,241,825 B2 | 7/2007 | Koga et al. |
| 7,247,143 B2 | 7/2007 | Law et al. |
| 7,671,974 B2 | 3/2010 | O'Mahony et al. |
| D623,302 S | 9/2010 | Barrett et al. |
| D625,824 S | 10/2010 | Brackett et al. |
| D630,536 S | 1/2011 | Pettit |
| D654,999 S | 2/2012 | Barrett et al. |
| 8,133,194 B2 | 3/2012 | Szamosfalvi et al. |
| 8,287,739 B2 | 10/2012 | Barrett et al. |
| 8,315,682 B2 | 11/2012 | Such et al. |
| 8,328,748 B2 | 12/2012 | Law et al. |
| 8,333,724 B2 | 12/2012 | Barrett et al. |
| D684,695 S | 6/2013 | Green et al. |
| D684,697 S | 6/2013 | Green et al. |
| 8,517,968 B2 | 8/2013 | Barrett et al. |
| D698,440 S | 1/2014 | Lombardi et al. |
| 9,002,655 B2 | 4/2015 | Bene |
| 2001/0016699 A1 | 8/2001 | Burbank et al. |
| 2001/0021817 A1 | 9/2001 | Brugger et al. |
| 2001/0037079 A1 | 11/2001 | Burbank et al. |
| 2001/0041892 A1 | 11/2001 | Burbank et al. |
| 2002/0103453 A1 | 8/2002 | Burbank et al. |
| 2002/0147423 A1 | 10/2002 | Burbank et al. |
| 2003/0009123 A1 | 1/2003 | Brugger et al. |
| 2003/0045784 A1 | 3/2003 | Palatnik et al. |
| 2003/0070969 A1 | 4/2003 | Muller et al. |
| 2003/0097087 A1 | 5/2003 | Gura |
| 2003/0143116 A1 | 7/2003 | Zheng et al. |
| 2003/0196949 A1 | 10/2003 | Sunohara et al. |
| 2003/0210390 A1 | 11/2003 | O'Mahoney et al. |
| 2003/0212316 A1 | 11/2003 | Leiden et al. |
| 2004/0087845 A1 | 5/2004 | Katarow et al. |
| 2005/0094127 A1 | 5/2005 | O'Mahony et al. |
| 2006/0036185 A1 | 2/2006 | Lewicke et al. |
| 2006/0144776 A1 | 7/2006 | Mishkin et al. |
| 2006/0226079 A1 | 10/2006 | Mori et al. |
| 2006/0290625 A1 | 12/2006 | Sugimoto |
| 2007/0015963 A1 | 1/2007 | Fengler et al. |
| 2007/0100219 A1 | 5/2007 | Sweitzer et al. |
| 2007/0149871 A1 | 6/2007 | Sarussi et al. |
| 2007/0179433 A1 | 8/2007 | Jonsson et al. |
| 2008/0081970 A1 | 4/2008 | Boyce et al. |
| 2008/0129047 A1 | 6/2008 | Blivet et al. |
| 2008/0300570 A1 | 12/2008 | Fowles et al. |
| 2009/0054751 A1 | 2/2009 | Babashan et al. |
| 2009/0247850 A1 | 10/2009 | Porges |
| 2010/0004518 A1 | 1/2010 | Vo et al. |
| 2010/0076364 A1 | 3/2010 | O'Mahony et al. |
| 2010/0110416 A1 | 5/2010 | Barrett et al. |
| 2010/0113891 A1 | 5/2010 | Barrett et al. |
| 2010/0168531 A1 | 7/2010 | Shaltis et al. |
| 2011/0004082 A1 | 1/2011 | Poeze et al. |
| 2011/0022077 A1 | 1/2011 | Green et al. |
| 2011/0160679 A1 | 6/2011 | Okiyama et al. |
| 2012/0120384 A1 | 5/2012 | Barrett et al. |
| 2012/0154789 A1 | 6/2012 | Barrett et al. |

FOREIGN PATENT DOCUMENTS

| | | |
|---|---|---|
| EP | 0 274 178 A1 | 7/1988 |
| EP | 467805 A1 | 1/1992 |
| EP | 0 990 444 A2 | 4/2000 |
| GB | 1 583 023 A | 1/1981 |
| JP | 56031085 A | 3/1981 |
| JP | 09-229847 | 9/1997 |
| JP | 2006199845 A | 8/2006 |
| JP | 2009-216711 | 9/2009 |
| WO | WO 93/06456 A1 | 4/1993 |
| WO | WO 93/06774 A1 | 4/1993 |
| WO | WO 94/27495 A1 | 12/1994 |
| WO | WO 98/37801 A1 | 9/1998 |
| WO | WO 00/33053 A1 | 6/2000 |
| WO | WO 01/87151 A2 | 11/2001 |
| WO | WO 01/93944 A1 | 12/2001 |
| WO | WO 02/078783 A2 | 10/2002 |

OTHER PUBLICATIONS

Original claims as filed for co-pending Canadian Patent Application No. 2,742,619 including a Voluntary Amendment dated Sep. 6, 2011.
Official action for co-pending European Patent Application No. 11 755 533.4 dated Apr. 16, 2013.
Official action for co-pending European Patent Application No. 11 754 974.1 dated Apr. 16, 2013.
International Search Report and Written Opinion for related International No. PCT/US2012/026637 dated Jun. 6, 2012).
Sacker-Berstein, Jonathan D., M.D., et al., "How Should Diuretic-Refractory Volume-Overloaded Heart Failure Patients Be Managed?", *The Journal of Invasive Cardiology*, vol. 15., No. 10 (Oct. 2003), pp. 585-590, retrieved from http;//www.medscape.com/viewarticle/463509_print on Mar. 11, 2013, pp. 1-11.
Jaski, Brian E., M.D., "Peripherally Inserted Veno-Venous Ultrafiltration for Rapid Treatment of Volume Overloaded Patients", *Journal of Cardiac Failure*, vol. 9, No. 3 (Jun. 2003) pp. 227-231.
Peer Review, "Effects of CPD and K2EDTA Preservatives on Blood Sample Hematocrit", *Asaio Abstract Submission Information*, 45th Annual Conference, San Diego, Jun. 3-5, 1999.
Cohen, Jennifer H., et al., "Hemoglobin Correction Factors for Estimating the Prevalence of Iron Deficiency Anemia in Pregnant Women Residing at High Altitudes in Bolivia", retrieved from http://www.scielo.php?script=sci_arttext&pid=S1020-49891999001100004 on Jun. 19, 2009 (12 pages).
Zhang, S., Ph.D., et al., Hematocrit Measurement Error Due to Time Dependence of Hematocrit fro EDTA-Preserved Blood Samples, *ANA 36 Annual Meeting & Scientific Exposition*, http//www.call4abstracts.com/ams/main/finalpreview, site visited Jun. 25, 2003.
Crit-Line Hematrocrt Accuracy Hema Metrics, vol. 1, *Tech Note* No. 11 (Rev D), pp. 1-4, Feb. 24, 2003.
*ScienceStockroom Flow Through Cuvette*, p. 8/14.
Blood Chamber 2001—Admitted Prior Art.
CL Photo 2000—Admitted Prior Art.
Blood Chamber Instruction Sheet 2001—Admitted Prior Art.
International Search Report of International Application No. PCT/US2011/061273 (Mar. 13, 2012).
Barrett, Lee, "Effects of CPD and $K_3$ EDTA Preservatives on Blood Sample Hematocrit", Abstract Submission, *ASAIO*, 45th Annual Conference, San Diego (Jun. 1999).
Written Opinion from International Application No. PCT/US2011/061273.
First Office action from foreign co-pending Chinese Patent Application No. 201180042991.4.
First Office action from foreign co-pending Chinese Patent Application No. 201180042991.4 dated May 21, 2014.
Official Action for European Patent Application No. 11 801 888.6 dated Jun. 5, 2014.
Office action for Australian Patent Application No. 2011299393 dated Jun. 27, 2013.

(56) References Cited

OTHER PUBLICATIONS

Official Action for European Patent Application No. 11 801 888.6 dated Apr. 25-14, 2014.
Official Action from co-pending Canadian Patent Application No. 2,742,619, dated Nov. 6, 2014 (5 pages).
Chinese Office action for Chinese Patent Application No. 201180055375.2, dated Mar. 16, 2015 (43 pages total).
Official Action for European Patent Application No. 11801888.6, dated Apr. 9, 2015.
Official Action for Chinese Patent Application No. 201280010099.2, dated Apr. 22, 2015.
Examination Report for Australian Application No. 2011329788, dated Jun. 17, 2015.
Japanese Office action for Japanese Patent Application No. 58245/2013, dated Dec. 24, 2014, (5 pages).
Chinese Office action for Chinese Patent Application No. 201180042991.4, dated Jan. 19, 2015, (9 pages).

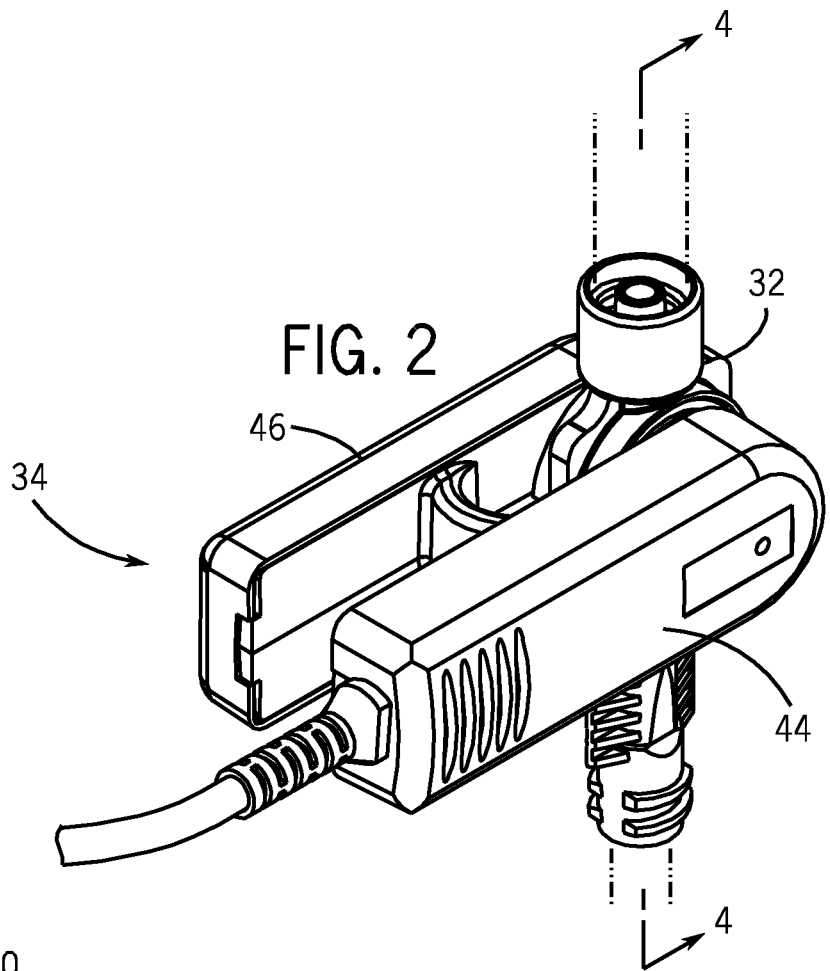
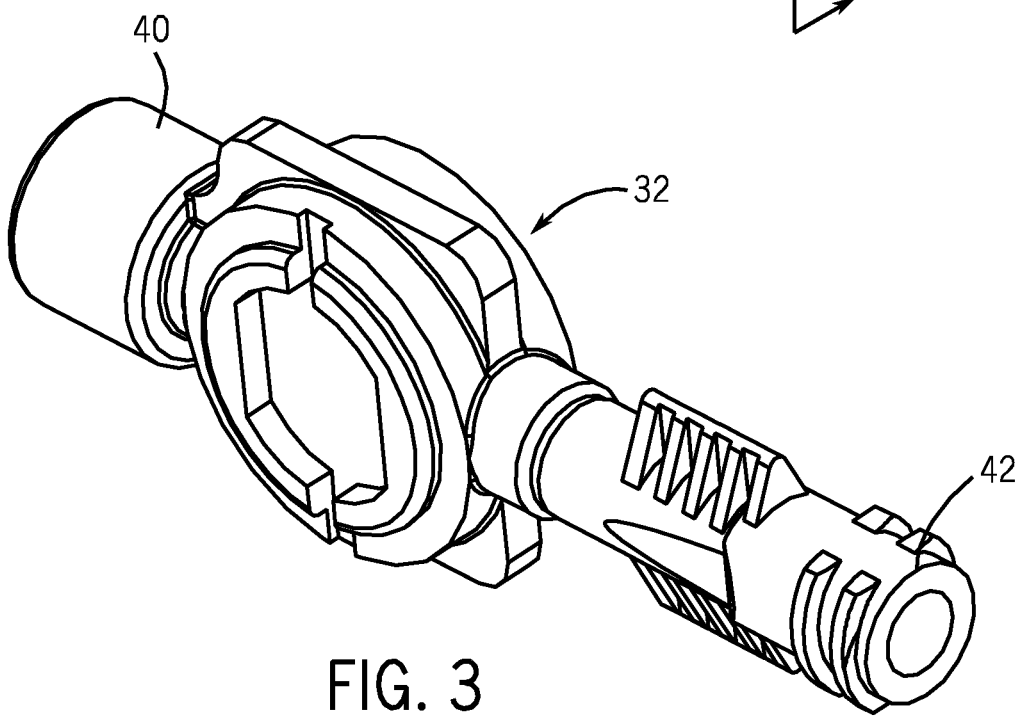

FIG. 9

Anemia Manager – Thursday, October 30, 2008 — 125

File  Setup  Help

Patients [1006 Argyle, Ryan] — 127   [Order by Name] — 129   [Get Data] — 131

Patient List | Patient Graph | Patient Management | Active Patients | Outside Boundries — 136
                132            130                            134

| PID | Boundaries | | Observed Hgb | | | ESA Dose | |
|---|---|---|---|---|---|---|---|
| | Low | High | Min | Max | Last | Last | Calculated |
| 1001 | 10.0 | 14.0 | 11.0 | 13.5 | 13.5 | 10199 | 7803 |
| 1002 | 10.0 | 14.0 | 11.7 | 13.6 | 13.3 | 10937 | 8073 |
| 1003 | 10.0 | 14.0 | 11.2 | 13.8 | 13.3 | 5186 | 3858 |
| 1004 | 10.0 | 14.0 | 11.7 | 13.8 | 12.4 | 1888 | 1449 |
| 1005 | 10.0 | 14.0 | 11.3 | 12.9 | 12.7 | 8926 | 6639 |
| 1006 | 10.0 | 14.0 | 11.4 | 13.5 | 12.9 | 2158 | 1571 |
| 1007 | 10.0 | 14.0 | 11.6 | 13.7 | 12.4 | 1658 | 1086 |
| 1008 | 10.0 | 14.0 | 11.5 | 14.0 | 12.5 | 6876 | 4974 |
| 1009 | 10.0 | 14.0 | 11.8 | 13.4 | 12.6 | 9493 | 7182 |
| 1010 | 10.0 | 14.0 | 11.4 | 13.8 | 13.5 | 3541 | 2514 |
| 1011 | 10.0 | 14.0 | 11.9 | 14.3 | 13.1 | 10009 | 7674 |
| 1012 | 10.0 | 14.0 | 11.6 | 12.9 | 12.2 | 4157 | 3502 |
| 1013 | 10.0 | 14.0 | 11.2 | 13.6 | 12.2 | 4054 | 2859 |
| 1014 | 10.0 | 14.0 | 12.5 | 13.8 | 13.1 | 9865 | 7563 |
| 1015 | 10.0 | 14.0 | 11.6 | 13.8 | 12.1 | 917 | 669 |
| 1016 | 10.0 | 14.0 | 11.8 | 14.4 | 12.2 | 1401 | 1019 |
| 1017 | 10.0 | 14.0 | 11.8 | 13.7 | 13.3 | 2042 | 1578 |
| 1018 | 10.0 | 14.0 | 9.2 | 11.0 | 9.4 | 4849 | 6032 |

137 → Anemia Manager – Thursday, October 30, 2008

File  Setup  Help

Patients [1006 Argyle, Ryan]  [Order by Name]  [Get Data]

Patient List | Patient Graph | Patient Manangement | Active Patients | Outside Boundries

| | Boundaries | | Observed Hgb | | | ESA Dose | |
|---|---|---|---|---|---|---|---|
| SID | PID | Low | High | Min | Max | Last | Last | Calculated |
| 11 | 1012 | 10.0 | 14.0 | 11.6 | 12.9 | 12.2 | 4157 | 3502 |
| 14 | 1013 | 10.0 | 14.0 | 11.2 | 13.6 | 12.2 | 4054 | 2859 |

Anemia Manager – Thursday, October 30, 2008 — 139

File  Setup  Help

Patients [1006 Argyle, Ryan]  [Order by Name]  [Get Data]

Patient List | Patient Graph | Patient Manangement | Active Patients | Outside Boundries

| | Boundaries | | Observed Hgb | | | ESA Dose | |
|---|---|---|---|---|---|---|---|
| PID | Low | High | Min | Max | Last | Last | Calculated |
| 1018 | 10.0 | 14.0 | 9.2 | 11.0 | 9.4 | 4849 | 6032 |
| 1056 | 10.0 | 14.0 | 9.2 | 11.1 | 9.7 | 815 | 1001 |
| 1073 | 10.0 | 14.0 | 9.1 | 11.4 | 9.4 | 8705 | 10842 |
| 1076 | 10.0 | 14.0 | 9.2 | 11.0 | 9.7 | 4252 | 5556 |
| 1077 | 10.0 | 14.0 | 9.2 | 11.2 | 9.4 | 4381 | 5327 |
| 1108 | 10.0 | 14.0 | 9.2 | 11.0 | 9.4 | 1581 | 2272 |
| 1122 | 10.0 | 14.0 | 11.6 | 14.2 | 14.2 | 7924 | 3913 |
| 1144 | 10.0 | 14.0 | 9.1 | 11.0 | 9.6 | 4164 | 4963 |
| 1157 | 10.0 | 14.0 | 9.1 | 11.2 | 9.7 | 9487 | 11978 |
| 1166 | 10.0 | 14.0 | 9.3 | 11.3 | 9.3 | 7900 | 9898 |
| 1169 | 10.0 | 14.0 | 9.1 | 11.2 | 9.6 | 8437 | 10316 |
| 1177 | 10.0 | 14.0 | 9.2 | 11.0 | 9.6 | 800 | 1152 |
| 1183 | 10.0 | 14.0 | 9.2 | 11.1 | 9.7 | 4449 | 5500 |
| 1202 | 10.0 | 14.0 | 9.2 | 12.2 | 9.6 | 4529 | 5468 |
| 1208 | 10.0 | 14.0 | 9.2 | 11.1 | 9.3 | 808 | 1052 |

HEMODIALYSIS PATIENT DATA ACQUISITION, MANAGEMENT AND ANALYSIS SYSTEM

FIELD OF THE INVENTION

The invention relates to data acquisition for hemodialysis patients, and the management and analysis of that data. In particular, it relates to the use of data taken at the onset of a series of scheduled hemodialysis treatment sessions for the patient, preferably gathered via a non-invasive, optical blood monitor. The invention enables the practical use of predictive algorithms to forecast an individual patient's blood condition in the future, e.g. a prediction of patient's hemoglobin level at next treatment session. Such prognostic data can be used to recommended therapeutic care, such as medication dosing. The invention is particularly useful for dosing anemia medication in hemodialysis patients, such as erythropoiesis stimulating agents (ESAs).

BACKGROUND OF THE INVENTION

Patients with kidney failure or partial kidney failure typically undergo hemodialysis treatment, often at a hemodialysis treatment center or clinic. When healthy, kidneys maintain the body's internal equilibrium of water and minerals (e.g., sodium, potassium, chloride, calcium, phosphorous, magnesium, and sulfate). The kidneys also function as part of the endocrine system to produce the hormone erythropoietin as well as other hormones. Hemodialysis is an imperfect treatment to replace kidney function, in part, because it does not correct the endocrine functions of the kidney.

In hemodialysis, blood is taken from a patient through an intake needle (or catheter) which draws blood from an artery located in a specific accepted access location (arm, thigh, subclavian, etc.). The drawn blood is pumped through extracorporeal tubing via a peristaltic pump, and then through a dialyzer which removes unwanted toxins such as blood urea, nitrogen, potassium, and excess water from the blood. As the blood passes through the dialyzer, it travels in straw-like tubes which serve as semi-permeable membrane passageways for the uncleaned blood. Fresh dialysate liquid, which is a solution of chemicals and water, flows through the dialyzer in the direction opposite the blood flow. As the dialysate flows through the dialyzer, it surrounds the straw-like membranes in the dialyzer. The fresh dialysate collects excess impurities passing through the straw-like tubes by diffusion, and also collects excess water through an ultrafiltration process due to a pressure drop across the membranes. The used dialysate exits the dialyzer with the excess fluids and toxins via an output tube, thus cleansing the blood flowing through the dialyzer. The dialyzed blood then flows out of the dialyzer via tubing and a needle (or catheter) back into the patient. Sometimes, a heparin drip or pump is provided along the extracorporeal blood flow loop in order to prevent clotting during the hemodialysis process. Several liters of excess fluid can be removed during a typical multi-hour treatment session. In the U.S., a chronic patient will normally undergo hemodialysis treatment in a dialysis center three times per week, either on Monday-Wednesday-Friday schedule or a Tuesday-Thursday-Saturday schedule.

Hemodialysis has an acute impact on the fluid balance of the body due in part to the rapid change in circulating blood volume. When the fluid removal rate is more rapid than the plasma refilling rate of the body, intravascular blood volume decreases. The resulting imbalance has been linked to complications such as hypotension, loss of consciousness, headaches, vomiting, dizziness and cramps experienced by the patient, both during and after dialysis treatments. Continuous quantitative measurement of parameters relating to the circulating blood volume (in real-time) during hemodialysis reduces the chance of dialysis-induced hypotension, and otherwise optimizes dialysis therapy regimes by controlling fluid balance and aiding in achieving the appropriate dry weight for the patient.

In the art, it is known that, during a hemodialysis treatment session, the change in hematocrit value is inversely proportional to the change in blood volume. For example, see U.S. Pat. No. 5,351,686 entitled "Disposable Extracorporeal Conduit For Blood Constituent Monitoring", assigned to the assignee of the present application and issuing on Oct. 4, 1994. The hematocrit value is the percentage of blood volume occupied by red blood cells. Since the number of red blood cells remains substantially constant during dialysis treatments that do not include bleeding or transfusions, the hematocrit will change only as a result of changing blood volume. Therefore, the change in blood volume during hemodialysis can be monitored by measuring hematocrit during the hemodialysis session.

There are several techniques to monitor hematocrit, although many are not practical for real-time monitoring during hemodialysis. The most common technique is a manual method in which a syringe is used to extract blood from the patient. The extracted blood is then put into a capillary device which is placed in a microcentrifuge. Because of the blood draw, this manual process is inadequate for monitoring real-time changes in blood volume during a hemodialysis treatment session. It has also been found to be somewhat inaccurate in practice. In addition, even if blood is drawn only a few times per week each blood draw lowers the patient iron level and induces further anemia. Therefore, in practice, hemodialysis patients normally have manual blood work done to determine hematocrit, as well as other blood abnormalities, about once a month.

Another device for measuring hematocrit is called a cell counter or Coulter counter. In a cell counter, a metered volume of blood is tested. The red blood cells are literally counted as they drop through a small diameter pipette within the cell counter. The mean cell volume of the red blood cells is measured via an electrical current that passes through a designated area of the pipette. The size of the blood cell correlates to the amount of electrical current passed. The volume of red blood cells is found by multiplying the red blood cell count times the mean cell volume. The hematocrit is determined by dividing the calculated red blood cell volume over the total volume of the sample. This method is assumed in the art to be more accurate than the microcentrifuge method. However, this method again requires that a blood sample be taken from the patient.

Another way to monitor hematocrit is to use a non-invasive, real-time optical blood monitor. The assignee of the present application manufactures such an optical blood monitoring system marketed under the name CRIT-LINE®. The CRIT-LINE® system continuously monitors the change in hematocrit over a dialysis session, and uses this information to calculate and display accurate percent blood volume change. It can also determine and display oxygen saturation levels and hemoglobin levels. The dynamic display of blood data during a hemodialysis session, including the display of change in blood volume, is quite helpful to attending staff administering the treatment to the patient.

To use the CRIT-LINE® system, a sterile, single-use blood chamber is attached, prior to hemodialysis treatment, inline in extracorporeal tubing on the arterial side of the dialyzer. The blood chamber provides a viewing point for optical sensors during the hemodialysis procedure. Multiple wavelengths of light are directed through the blood chamber and the patient's blood flowing therethrough, and photo detectors detect the resulting intensity of each wavelength. The preferred wavelengths are about 810 nanometers, which is substantially isobectic for red blood cells containing hemoglobin, and about 1300 nanometers, which is substantially isobectic for water. A ratiometric technique implemented in the CRIT-LINE® controller, as substantially disclosed in U.S. Pat. No. 5,372,136 entitled "System And Method For Non-invasive Hematocrit Monitoring", which issued on Dec. 13, 1999 and is also assigned to the assignee of the present application, uses this information to calculate the patient's hematocrit value (HCT) in real-time, which as mentioned is the percentage of blood volume that is occupied by red blood cells. The CRIT-LINE® monitor provides an absolute measurement of hematocrit in real-time that is independent of other blood analytes. One of the advantages of monitoring the patient's blood non-invasively is that it is not necessary to take a blood draw, and therefore the anemic condition is not exacerbated.

The CRIT-LINE® monitor estimates patient hemoglobin levels (Hgb) from the measured hematocrit value. Hemoglobin levels are expressed as the amount of hemoglobin in grams (gm) per deciliter (dl) of whole blood. The most common direct method of measuring hemoglobin requires the extraction of a blood sample from the patient, and then treating the blood with a lysing agent in the laboratory in order to rupture the red blood cell membranes and release the hemoglobin into solution so that its concentration can be measured. Obviously, this technique cannot be implemented in real-time in the CRIT-LINE® monitor. Rather, the CRIT-LINE® system estimates real-time hemoglobin level based on the measured real-time hematocrit level (e.g. HCT=2.941 Hgb).

Oxygen saturation (SAT) measures the percentage of hemoglobin binding sites occupied by oxygen. Hematocrit independent oxygen saturation is measured in the CRIT-LINE® monitor using a photo emitter having a wavelength of about 660 nanometers. The photo detector monitors the intensity of 660 nm light after it passes through the blood chamber and the blood flowing through the blood chamber. A ratiometric model using the intensity of detected light at 660 nm and at substantially 810 nm is used to determine the real-time oxygen saturation level in the CRIT-LINE® monitor.

The CRIT-LINE® monitor is thus able to non-invasively monitor in real-time during hemodialysis the patient's hematocrit (HCT), change in blood volume (BVΔ), oxygen saturation (SAT), and calculated hemoglobin (Hgb) levels.

Hemodialysis centers normally include several hemodialysis systems so that multiple patients can be treated contemporaneously. In many centers, a dedicated CRIT-LINE® monitor is used in connection with each individual hemodialysis system. The display on the CRIT-LINE® monitor (which is normally located next to the patient) helps the attending nurses insure that hematocrit, oxygen saturation, and blood volume levels, as well as calculated hemoglobin levels, remain within the accepted tolerances for the treated patient. The patient data, such as hematocrit, oxygen saturation, and calculated hemoglobin values, is often downloaded to a host computer for patient records.

As kidney function decreases, one of the side effects is that erythropoietin synthesis decreases, which can potentially lead to anemia, causing fatigue in the patient. Hemoglobin variability is common in patients with End Stage Renal Disease (ESRD) on hemodialysis. Erythropoiesis stimulating agents (e.g., recombinant erythropoietin), commonly known as ESAs, are pharmaceutically produced and administered by physicians to hemodialysis patients in order to manage anemia when present. Recombinant ESA can be administered either subcutaneously via syringe, or via a drip in the extracorporeal tubing of the hemodialysis loop, normally at the end of a hemodialysis treatment session. The purpose of administering ESA is to maintain the patient's hemoglobin levels within a healthy range. Under dosing ESA results in low hemoglobin levels. On the other hand, overuse of ESA can result in excessive cost, as well as undesirable side effects.

SUMMARY OF THE INVENTION

In one aspect, the invention is a hemodialysis patient data acquisition and management system that receives data collected by one or more non-invasive, optical hemodialysis blood monitors, and in particular, downloads data collected at the onset of a patient's hemodialysis treatment sessions to a host computer.

A database on the host computer contains historical session commencement data for a large number of patients (e.g. 250 patients). Software on the host computer displays historical data for a selected patient. It is preferred that at least some of the data be displayed graphically, perhaps using trend lines as well as clear indications of maximum and minimum desired values of monitored data, such as $Hgb_i$, $HCT_i$, $SAT_i$. The purpose of the database is to provide the attending physician and/or nurse with historical information on the patient to facilitate therapeutic care for the patient.

It is notable that the downloaded data relates to the blood characteristics taken at the onset of the hemodialysis treatment session before the dynamics of the hemodialysis treatment begins to affect the patient. Once the hemodialysis treatment begins, blood data changes significantly. The purpose of this aspect of the invention is to collect blood data on the patient, during the stable regime of the blood reflecting the patient's true fluid condition, on a recurring basis in order to facilitate long-term analysis of the patient.

The preferred non-invasive, optical blood monitor includes an optical sensor assembly that monitors the patient's blood flowing through extracorporeal tubing in a hemodialysis system. The sensor assembly comprises a blood chamber connected in-line in the extracorporeal tubing, and a plurality of photo emitters emitting light at various wavelengths as well as one or more photo detectors for sensing the intensity of the light at each wavelength after it passes through the blood chamber and the patient's blood flowing through the blood chamber. The optical blood monitor also includes a controller that receives data signals from the one or more photo detectors, and also generates commencement session data for the patient undergoing hemodialysis treatment. The commencement session data includes at least an identification code for the patient, and measured blood data taken at the onset of the treatment session, such as initial values for hematocrit ($HCT_i$); hemoglobin ($Hgb_i$); oxygen saturation ($SAT_i$). In accordance with this aspect of the invention, the controller for each blood monitor communicates with a host computer, preferably via a wireless network. Whenever a blood monitor in the network becomes active, session commencement data from the blood monitor is automatically downloaded along with corresponding patient identification code from the respective blood monitor to the host computer. In this manner, the system is able to collect patient data taken at the onset of treatment sessions automatically. Ongoing data is collected on a recurring basis every two to three days as each patient is treated.

The system also allows data to be entered manually. This may be useful in situations where one or more hemodialysis systems in a clinic are not set up with an optical blood monitor or when the communication block to a monitor is inoperative. In such situations, a blood sample may be taken from the patient before selected treatment sessions (e.g., on a monthly basis). Information such as hematocrit and hemoglobin levels determined from blood work done on the sample may be entered manually into the host computer. Of course, data automatically downloaded from an optical blood monitor every two to three days taken at the onset of each treatment session provides much more complete historical information than monthly data taken manually, thereby allowing for earlier detection of the trends and alerting attending medical staff to changes in a patient's condition sooner.

In another aspect of the invention, the host computer contains software implementing a predictive algorithm for predicting the patient's hemoglobin level at the start of his or her next scheduled treatment session. Such a predictive algorithm is particularly useful for managing therapeutic care for patients with anemia. The preferred predictive algorithm for Hgb is as follows:

Predicted Hgb Value=0.4784356 (Hgb of Last Period)+0.2042212 (Hgb of Second to Last Period)+0.222685 (Hgb of Third to Last Period)+ 0.0000396 (Last ESA Dose value)+0.9627966 where Hgb of last period, Hgb of second to last period and Hgb of the third to last period represent the patient's hemoglobin levels monitored at the previous three hemodialysis treatment sessions, the last ESA dose value represents the ESA dose administered to the patient at the patient's last treatment session, and the predicted Hgb value represents the predicted value of the patient's hemoglobin level at the start of the next treatment session.

The predictive algorithm provides the attending physician with a statistically accurate prediction of the patient's hemoglobin level at the start of the patient's next scheduled treatment session, based on data collected for the previous and current treatment sessions along with the corresponding ESA dosing in place. The algorithm is quite robust when the data is collected on an every two to three day period, which is possible with the automatic collection of session commencement data using an optical blood monitor as described above.

As mentioned, it is preferred that the predicted hemoglobin level be used by the system to determine a recommended dosage for an anemia management drug. For example, in a particularly preferred embodiment of the invention, the software on the host computer also includes protocol for calculating an ESA dosage recommendation, based at least in part on historical hemoglobin values for the patient stored in the patient database, and in part on the predicted hemoglobin value for the patient at the next treatment session.

The invention thus provides a number of tools for improving the probability that hemodialysis patients attain Hgb levels within their target hemoglobin range at the start of the next scheduled treatment session.

Other features and objects of the invention may be apparent to those skilled in the art upon reviewing the following drawings and description thereof.

BRIEF DESCRIPTION OF THE DRAWINGS

FIG. 2 is a perspective view showing an optical sensor assembly for the blood monitor positioned to sense blood flowing through a blood chamber connected in the extracorporeal tubing of the hemodialysis system.

FIG. 3 is a detailed view of the blood chamber shown in FIG. 2.

FIGS. 9-13 depict the preferred graphical user interface appearing on a host computer running software to implement the preferred embodiment of the invention.

DETAILED DESCRIPTION OF THE DRAWINGS

Figure 1:
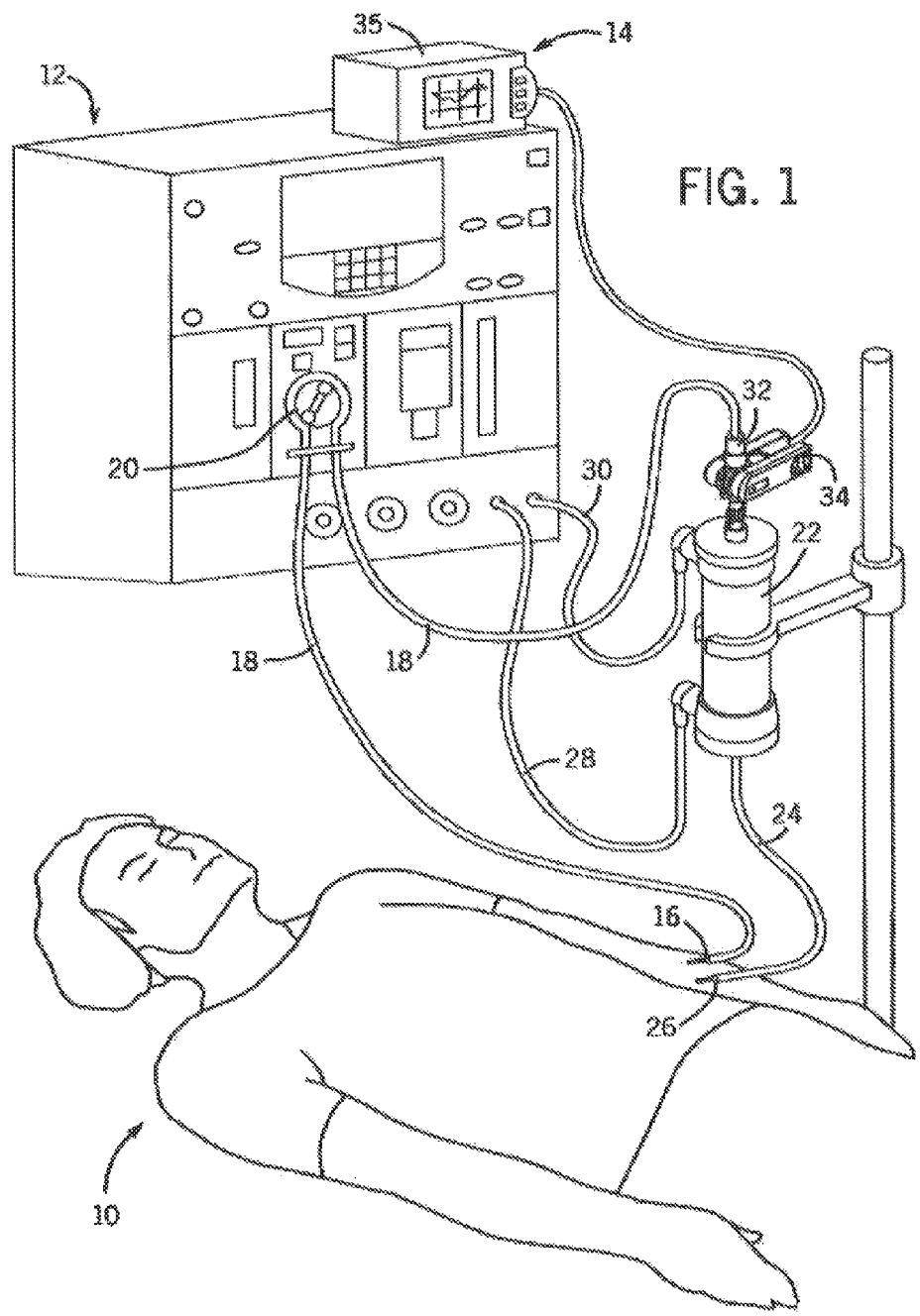
FIG. 1 is a perspective view of a typical patient undergoing hemodialysis treatment with a non-invasive, optical blood monitor monitoring the patient's blood in real-time as it passes through extracorporeal tubing in the hemodialysis system.

FIG. 1 illustrates a patient 10 undergoing hemodialysis treatment using a conventional hemodialysis system 12, as well as a non-invasive, optical blood monitor 14. A typical hemodialysis clinic will have several hemodialysis systems 12 for treating patients on a Monday-Wednesday-Friday schedule or a Tuesday-Thursday-Saturday schedule. While the invention is not limited to the number of hemodialysis systems located at a clinic, or the specific type of hemodialysis system, the general operation of the hemodialysis system 12 is helpful for understanding the environment in which the invention is intended to operate.

An input needle or catheter 16 is inserted into an access site of the patient 10, such as in the arm, and is connected to extracorporeal tubing 18 that leads to a peristaltic pump 20 and then to a dialyzer or blood filter 22. The dialyzer 22 removes toxins and excess fluid from the patient's blood. The dialysized blood is returned from the dialyzer through extracorporeal tubing 24 and return needle or catheter 26. In some parts of the world, the extracorporeal blood flow may receive a heparin drip to prevent clotting although that is not shown in FIG. 1. The excess fluids and toxins are removed by clean dialysate liquid which is supplied to the dialyzer 22 via tube 28 and removed for disposal via tube 30. A typical hemodialysis treatment session takes about 3 to 5 hours in the United States.

The optical blood monitor 14 includes a blood chamber 32, an optical blood sensor assembly 34, and a controller 35. The blood chamber 32 is preferably located in line with the extracorporeal tubing 18 upstream of the dialyzer 22. Blood from the peristaltic pump 20 flows through the tubing 18 into the blood chamber 32. The preferred sensor assembly 34 includes LED photo emitters that emit light at substantially 810 nm, which is isobestic for red blood cell hemoglobin, substantially 1300 nm, which is isobestic for water, and at substantially 660 nm, which is sensitive for oxygenated hemoglobin. The blood chamber 32 includes lenses so that the sensor emitters and detectors can view the blood flowing through the blood chamber 32, and determine the patient's real-time hematocrit value and oxygen saturation value using ratiometric techniques generally known in the prior art. The preferred ratiometric model is described in more detail in copending patent application entitled "Measuring Hematocrit And Estimating Hemoglobin Values With An Optical Blood Monitoring System", filed on even date herewith by Louis Barrett, David Peterson, Kristian Sammann, this co-pending patent application being incorporated in its entirety herein. The incorporated copending patent application also describes a method of scaling output values for hematocrit (HCT) to account for differences in preservatives used to calibrate optical monitoring equipment and other equipment typically used in the clinic when taking blood samples from patients. It is contemplated that the preferred embodiment of the invention utilize the method of scaling hematocrit values, as discussed in the above-incorporated patent application.

Figure 4:
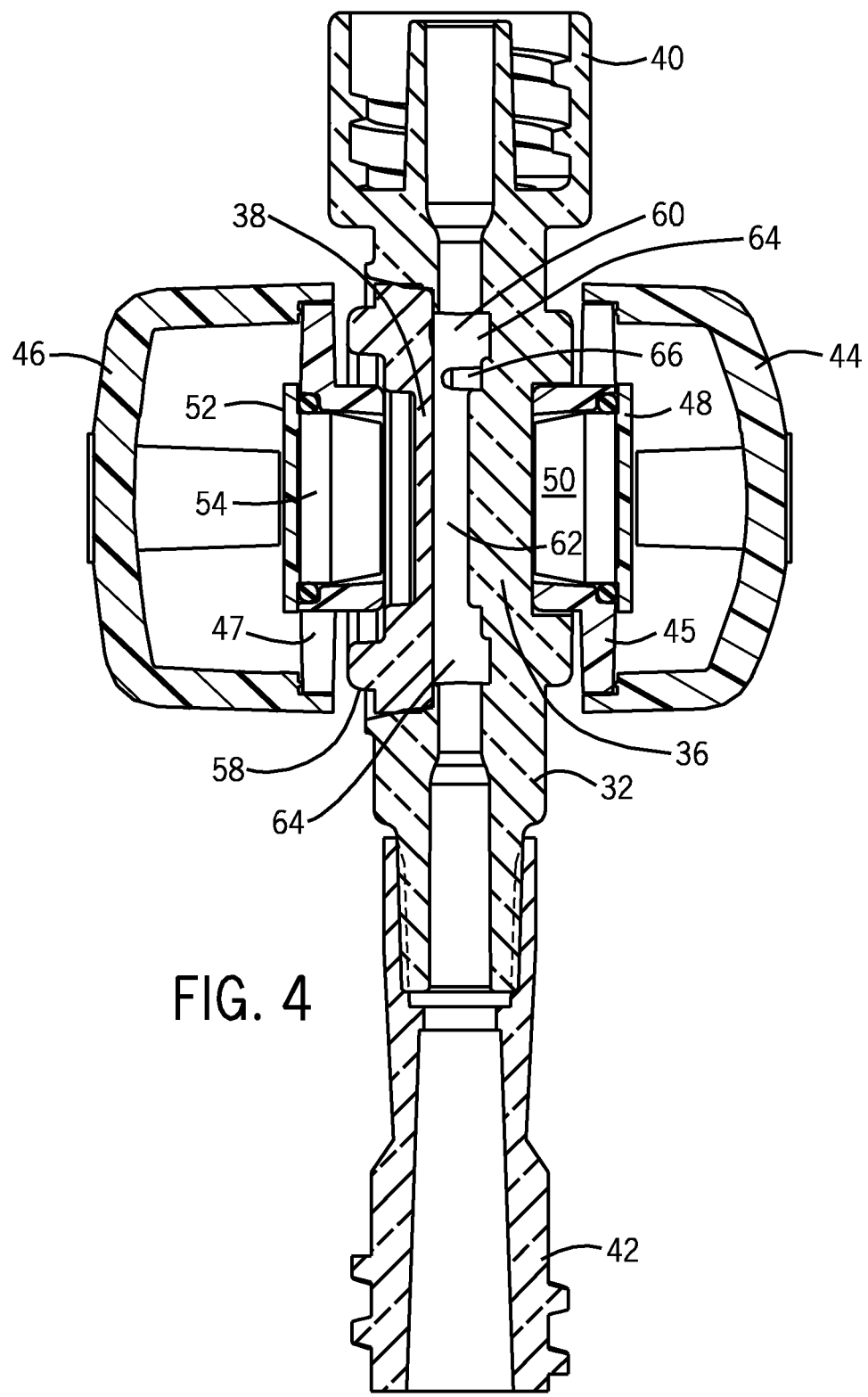
FIG. 4 is a cross-sectional view taken along line 4-4 in FIG. 2.

Referring to now FIGS. 2-4, the body of the blood chamber 32 is preferably made of molded polycarbonate. It includes two viewing windows 36, 38 (see FIG. 4). The inlet 40 and outlet 42 are designed to be compatible with standard medical industry connecting devices, conventionally known as Luer locks. In the blood chamber 32 shown in the drawings, the inlet 40 is integrally molded with the blood chamber 32, whereas the outlet 42 consists of a suitable off-the-shelf connection adapter glued to the body of the blood chamber 32. The sensor assembly 34 includes an emitter subassembly 44 and a detector subassembly 46. As best shown in FIG. 4, an emitter circuit board 48 containing LEDs emitting light at substantially 660 nm, 810 nm and 1300 nm, is mounted within the housing for the sensor subassembly 44. The LED circuit board 48 emits light through a lens 50 that is mounted between the circuit board 48 and the viewing window 36 for the blood chamber 32. The controller 35 controls the operation of each of the respective LED emitters and/or detectors so as to de-commutate the independent wavelength measurements. Another circuit board 52 containing light detectors, one made of silicon to detect light intensity at 810 nm and 660 nm, and the other made of InGaAs to detect light intensity at 1300 nm. The detector circuit board 52 is mounted within the housing for the detector subassembly 46. A lens 54 is mounted between the detector circuit board 52 and the viewing window 38 in the blood chamber 32 in order to facilitate transmission of light at the respective wavelengths to the detectors on the circuit board 52. Note that the viewing window 38 is molded into a separate insert 58 that is sonically welded to the body of the blood chamber 32. As in the prior art, the blood flows from the inlet 40 through the passageway 60 to a central viewing region 62. The light at the three selected wavelengths, namely 810 nm, 1300 nm and 660 nm, are transmitted through the blood flowing through this portion 62 of the blood flow path, as well as the viewing windows 36, 38 in the chamber 32. The viewing region 62 provides a substantially flat, thin (e.g. less than 0.1 inches) viewing region for the blood flowing through the blood chamber 36. A moat 64 surrounds the flat viewing region 62. The moat 64 is somewhat deeper than the flat viewing region 62, and serves to distribute the flow evenly and steadily through the viewing region. It also serves to reduce errant light piping through the polycarbonate blood chamber 32 from the emitters 48 to the detectors 52 due to the higher concentration of blood surrounding the viewing area 62. One or more protrusions 66 are located immediately upstream of the viewing region 62 so that the flow across the viewing region 62 is at least somewhat turbulent. While the flow across the viewing region 62 is preferably somewhat turbulent, the configuration of the blood chamber 32 shown in FIG. 4 results in a steady state flow through the viewing region 62 in terms of pressure and flow rate.

The housings 44 and 46 for the sensor assembly 34 include an inner housing piece 45, 47 which connects to the outer shells 44, 46. The inner housing components 45, 47 provide an opening into which the lenses 50, 54 are mounted. The sensor assembly 34 is preferably a spring loaded clip that can be mounted to the blood chamber 32, as shown in FIG. 2. Both sides of the blood chamber 32 are molded such that the clip 34 will reside in a predetermined position when mounted to the blood chamber 32. As mentioned, blood chamber 32 is a single use, reusable polycarbonate component. Between patients, the blood chamber 32 is replaced as is the extracorporeal tubing 18, 24, and blood filter 22.

Figure 5:
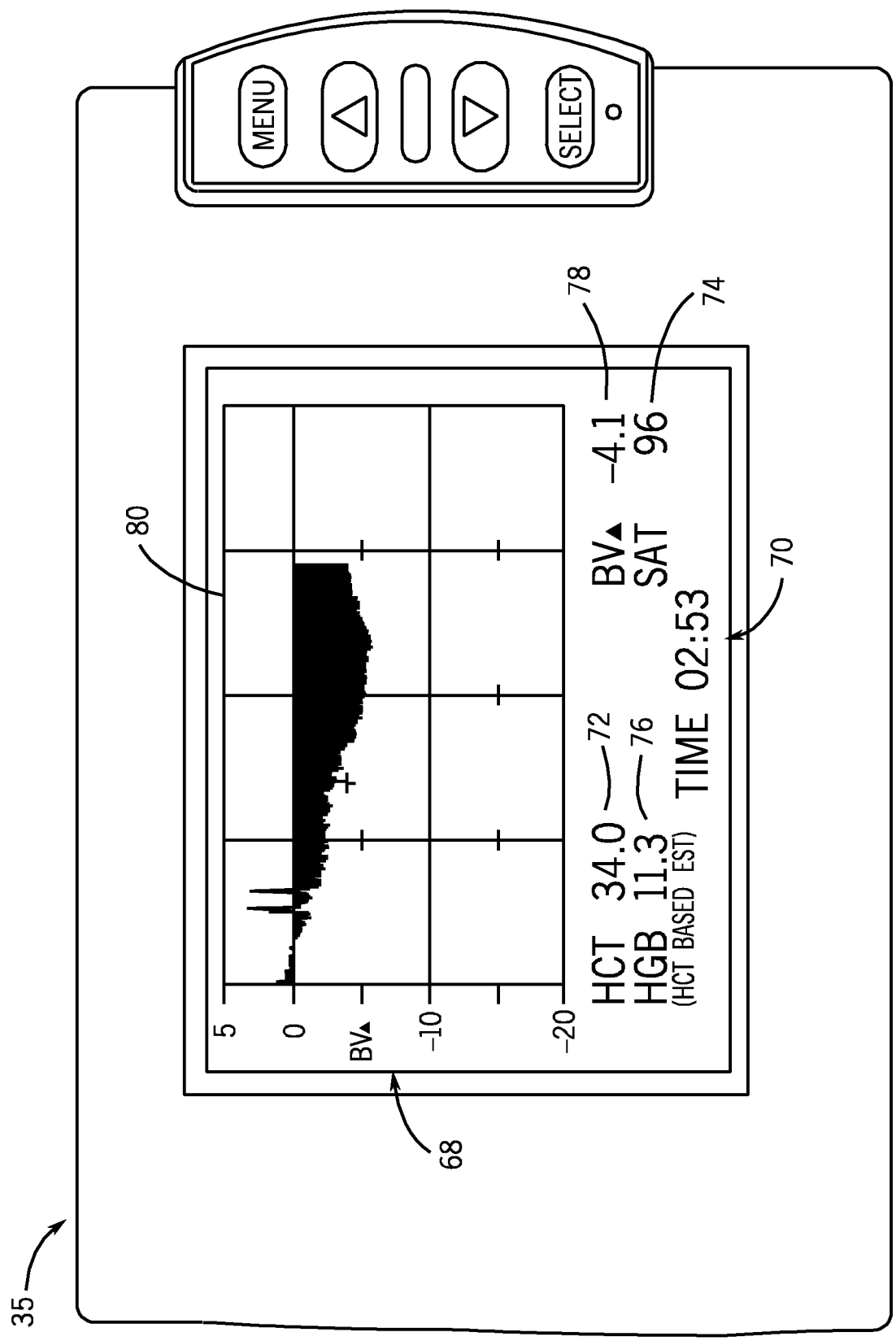
FIG. 5 is a front elevational view of the controller for the optical blood monitor illustrating displayed data including real-time hematocrit (HCT), change in blood volume (BVΔ), hemoglobin (HGB), and oxygen saturation (SAT) levels, as well as the amount of time into the hemodialysis treatment session and a graphical representation of the change in blood volume during the course of the hemodialysis treatment session.

FIG. 5 is a front elevational view of the preferred controller 35 for the optical blood monitor 14. The controller 35 includes a display 68 which provides real-time blood monitoring data for the patient undergoing hemodialysis. The display in FIG. 5 illustrates the amount of time 70 that the patient 10 has been monitored while undergoing hemodialysis for the current treatment session. The time 70 displayed on the screen 68 in FIG. 5 is 2 hours and 53 minutes. The display 68 also illustrates real-time values for the optically monitored hematocrit (HCT) 72 and oxygen saturation (SAT) level 74, as well as the calculated values for hemoglobin (HGB) 76 and change in blood volume (BVΔ) during the treatment session 78. The graph 80 on the display 68 illustrates the change in the patient's blood volume, HCT, or $O_2$SAT (as selected by Menu option) over the course of the 2 hour and 53 minute monitoring session. This data is displayed, as shown in FIG. 1, in a location that is located within the vicinity of the patient 10.

The preferred controller 35 for the optical blood monitor 14 contains an internal real-time clock that continuously registers time and date, and includes battery backup when it is off. The clock is preferably set at the factory, although it may be desirable to correct the time upon initial installation or for daylight savings time changes, etc. Periodically, the calibration and accuracy of the optical blood monitor 14 should be checked. In the art, this is normally done by placing the sensor clip 34 onto a verification filter (made of layered plastic having known optical qualities) that is mounted to the side of the monitor 14. Calibration software within the controller 35 will verify the calibration of the unit, or allow the user to field calibrate the unit within specified limits to bring it back to factory calibration settings. If the specified adjustment limits are exceeded, it is necessary to return the unit to the factory for calibration.

For purposes of background, when a typical patient 10 arrives at a hemodialysis clinic, the patient is first checked in and then weighed on a scale at the clinic. The patient then is seated in an assigned hemodialysis chair where a clinician inserts an arterial and venous needle into the patient's access. The access may be an artificial shunt or a natural fistula that has been surgically tied from an artery to a vein. Alternatively, as mentioned previously, the connection might be through a catheter. Next, the dialysis lines 18, 24 are prefilled with normal saline and connected to the patient. The peristaltic pump 20 is started slowly and the normal saline is flushed through the lines 18, 24 as well as the dialyzer 22 into the patient 10, as arterial blood is pulled into the dialysis circuit. The normal saline tends to lubricate or prime the system for blood passage. Also, since saline is less dense than blood, any leaks in the system will be immediately apparent.

The clinician then waits approximately 5 minutes for the hematocrit (HCT) of the patient's body to stabilize after the saline has been infused. The saline must mix out in the patient's body in order to obtain a stable reading for the initial hematocrit (HCT) at the onset of the hemodialysis process. During this wait time, the clinician presses the menu button on the monitor 14 and enters the patient ID number. While it would be technically possible to enter the patient's name in lieu of a patient ID number, it is preferable to enter a patient ID number in order to accommodate patient privacy laws. Once approximately 5 minutes have passed after the saline prime is flushed into the body, the patient's data run begins. The optical blood monitor 14 is turned on to measure and store in memory initial values for hematocrit ($HCT_i$), hemoglobin ($Hgb_i$), and oxygen saturation ($SAT_i$) levels. As mentioned, the hemoglobin level is estimated from the measured hematocrit (HCT=2.941*Hgb at sea level). As also mentioned, the hemoglobin level is preferably scaled according to the disclosure in the above mentioned copending patent application which has been incorporated herein by reference.

After the initial levels for hematocrit, hemoglobin and oxygen saturation are measured and stored in the controller 35, the ultra filtration rate (UFR) on the dialysis machine is advanced, causing an osmosis vacuum to form across the dialyzer 22. From that point on, fluid is removed from the blood, but red blood cells are preserved within the body. In the controller 35 for the blood monitor, the real-time data is updated in the memory and on the screen at a rate of one sample per minute for each of the displayed parameters. Real-time data is available at the serial port at a regular sample rate for external data collection use.

At the end of treatment, the menu button on the controller 35 is pressed and an option to stop the treatment session is selected. A printer can be connected to the monitor for printing graphs of HCT, BVΔ, and SAT.

The hemodialysis system 12 is stopped after the blood is drained from the lines into the venous needle 26 of the patient 10. The patient is allowed to sit for a while, and the clinical staff assesses the patient's conditions while they remove the needles and bandage the patient. The patient is then weighed again at the end of the treatment, and perhaps a physician prescribes the administration of an ESA dose. The patient 10 then receives their prescribed dose and is released to go.

Preferably, the controller 35 is set up so that the memory of the patients' data for the day's treatment sessions are protected and must be deliberately cleared before the controller 35 is ready to monitor subsequent treatments on the hemodialysis system 12. Also held in memory in the controller 35 are the initial values $HCT_i$, $Hgb_i$, $SAT_i$ and a time and date stamp, for the commencement of the patient's treatment session. This set of session commencement data ($HCT_i$, $Hgb_i$, $SAT_i$, time and date stamp) is the subject of one aspect of the present invention, which is described in more detail below with respect to FIGS. 7 through 10.

Another aspect of the invention involves the use of a predictive algorithm for estimating the patient's hemoglobin level at his or her next treatment session. Data was collected from 43 hemodialysis patients over the course of 15 months. The data collected included optically detected hemoglobin levels (Hgb) collected at the beginning of each patient's treatment session. In addition, from time to time, blood samples were taken, and hemoglobin levels for the patients were taken based on ordinary lab work. The optical blood monitor in the test estimated hemoglobin levels based on optically measured HCT.

While 43 different patients were monitored at the beginning of their scheduled hemodialysis treatment sessions, not all of the patients attended each of their scheduled hemodialysis sessions. The average number of treatment sessions being monitored per patient was 151.7, with the minimum number of observations being 119 per patient and the maximum being 188 per patient. The data were fit with a cross-sectional regression model, having the following format:

$$\text{Predicted Hgb Value} = 0.4784356 \text{ (Hgb of Last Period)} + 0.2042212 \text{ (Hgb of Second to Last Period)} + 0.222685 \text{ (Hgb of Third to Last Period)} + 0.0000396 \text{ (Last ESA Dose value)} + 0.9627966 \quad \text{Eq. (1)}$$

where Hgb of last period, Hgb of second to last period and Hgb of the third to last period represent the patient's hemoglobin levels (gm/dl) monitored at the previous three treatment sessions, and the last ESA dose value represents the ESA dose (International Units) administered to the patient at the patient's last treatment session, and the predicted Hgb value represents the predicted value of the patient's hemoglobin level at the start of the next scheduled treatment session. The inventors have found that three lag periods provides the best fit for the cross-sectional regression model. Of course, the coefficients in the cross-sectional regression model would likely change at least somewhat depending on the number of observations and the condition of the various patients in the test pool. It should be noted that other factors were monitored during the test, but no significant statistical correlation appeared to exist, for example, with the patient's MAP, average trans SAT, or Ferritin levels and or the patient's dry weight.

A cross-sectional regression model was chosen to model the collected data, in contrast to a regulated linear regression, because the data was expected to be statistically correlated. In other words, data points relating to a particular patient were not expected to be independent of other data points for that patient. Due to this expected correlation, a cross-sectional regression model is preferred with respect to a linear regression in a model. Nevertheless, collected data is likely to be adequately fit by other types of statistical models as well, such as a time series model like a constant coefficient single exponential smoothing model. Broadly speaking, this aspect of the invention may be implemented using a variety of statistical models.

Table 1 illustrates the statistical accuracy of the cross-sectional regression model of Eq. (1) to the data collected.

TABLE 1

| Variable; Based on 43 Patients, 6537 observations (mean of 152 observations per patient) | Coefficient | Standard Error | 95% Confidence Interval | P-Value |
|---|---|---|---|---|
| Optical Hgb of last time period | 0.4784356 | 0.0120666 | (0.455, 0.502) | <0.001 |
| Optical Hgb of second to last time period | 0.2042212 | 0.0131147 | (0.179, 0.230) | <0.001 |
| Optical Hgb of third to last time period | 0.222685 | 0.0120086 | (0.199, 0.246) | <0.001 |

TABLE 1-continued

| Variable; Based on 43 Patients, 6537 observations (mean of 152 observations per patient) | Coefficient | Standard Error | 95% Confidence Interval | P-Value |
|---|---|---|---|---|
| ESA Dose (In international units) of last time period | 0.0000396 | 3.58e−06 | (3.260E−05, 4.670E−05) | <0.001 |
| Constant | 0.9627966 | 0.0777629 | (0.810, 1.115) | <0.001 |

Figure 6:
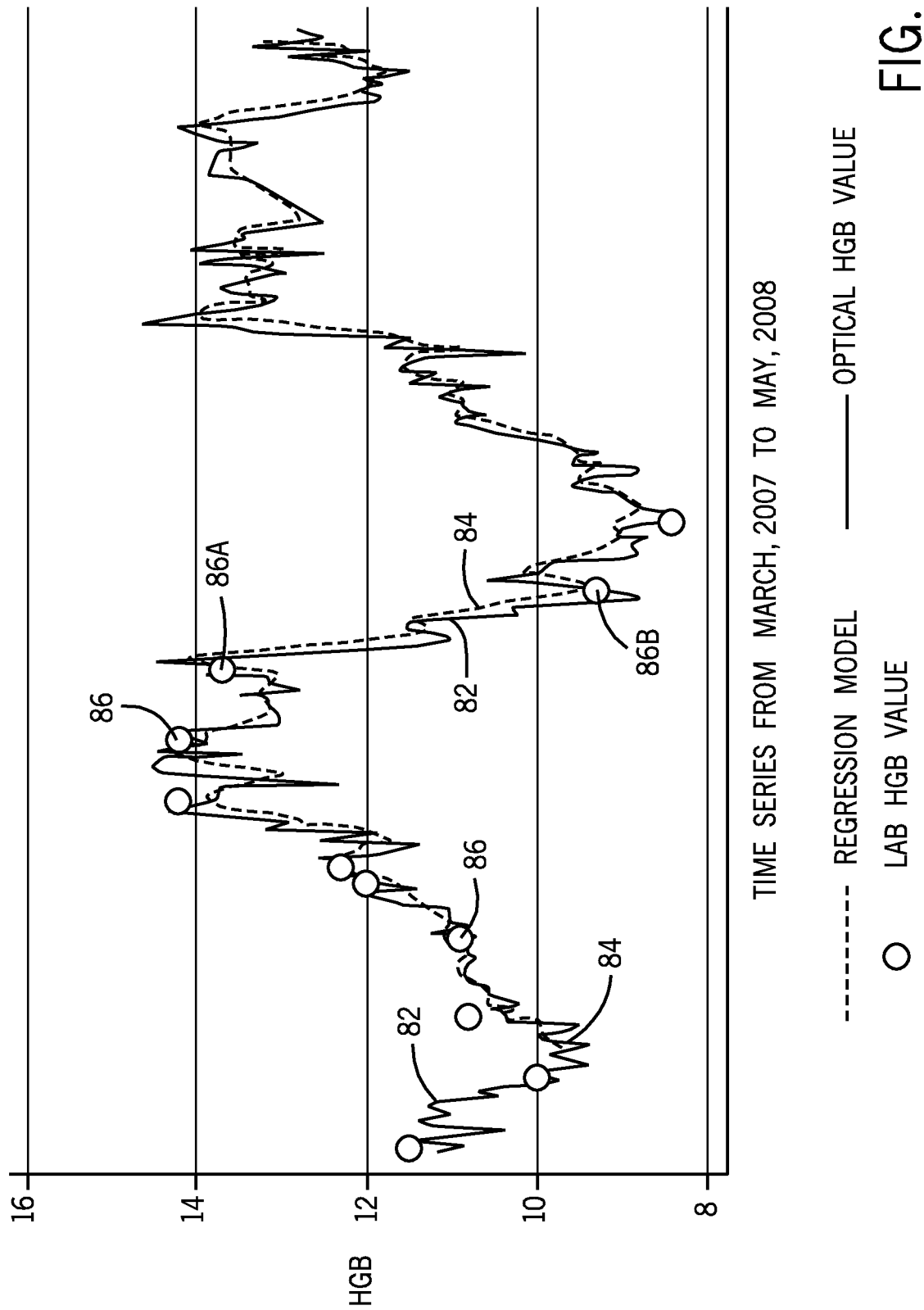
FIG. 6 is a time series plot of data for a representative patient taken at the onset of a series of reoccurring hemodialysis treatment sessions by an optical blood monitor, which also shows monthly hemoglobin data from manual lab work for the representative patient, as well as historical results of a predictive algorithm for estimating the patient's hemoglobin level at the next treatment session.

FIG. 6 is a plot of data from a representative patient, showing the patient's hemoglobin level at the onset of hemodialysis treatment sessions over a 15 month period. The solid line 82 in FIG. 6 tracks optically monitored hemoglobin values ($HCT_i$) which are collected by an optical blood monitor 14 monitoring the patient during a series of scheduled hemodialysis treatment sessions. The hemodialysis treatment sessions were scheduled to occur three times a week. The dashed line 84 plots the predicted values from the cross-sectional regression model. Note that the dashed line 84 does not begin until several optically measured data points are available (i.e. line 82). The circles 86 identify the patient's hemoglobin data as taken from a blood sample and determined in a laboratory. Referring to reference numbers 86a and 86b, it is important to note that a patient's hemoglobin values can change substantially between the time that a patient normally obtains blood work from a laboratory (e.g. on a monthly basis). The difference between data point 86a and data point 86b is over three grams per deciliter. On the other hand, the optical blood monitor 14 is able to monitor the patient's hemoglobin level on a more frequent basis. As shown in FIG. 6, the regression model 84 closely tracks the actual data 82 collected by the optical blood monitor. Of course, the regression model 84 is somewhat smoothing, and therefore its forecast is resistant to noise in the data signal. In any event, the hemoglobin values predicted by the regression model 84 are quite consistently accurate, as shown in FIG. 6, with both the optically monitored hemoglobin levels and the hemoglobin levels determined via lab work. Further, use of the predictive hemoglobin algorithm helps staff to maintain a more constant hemoglobin level for the patient.

Figure 7:
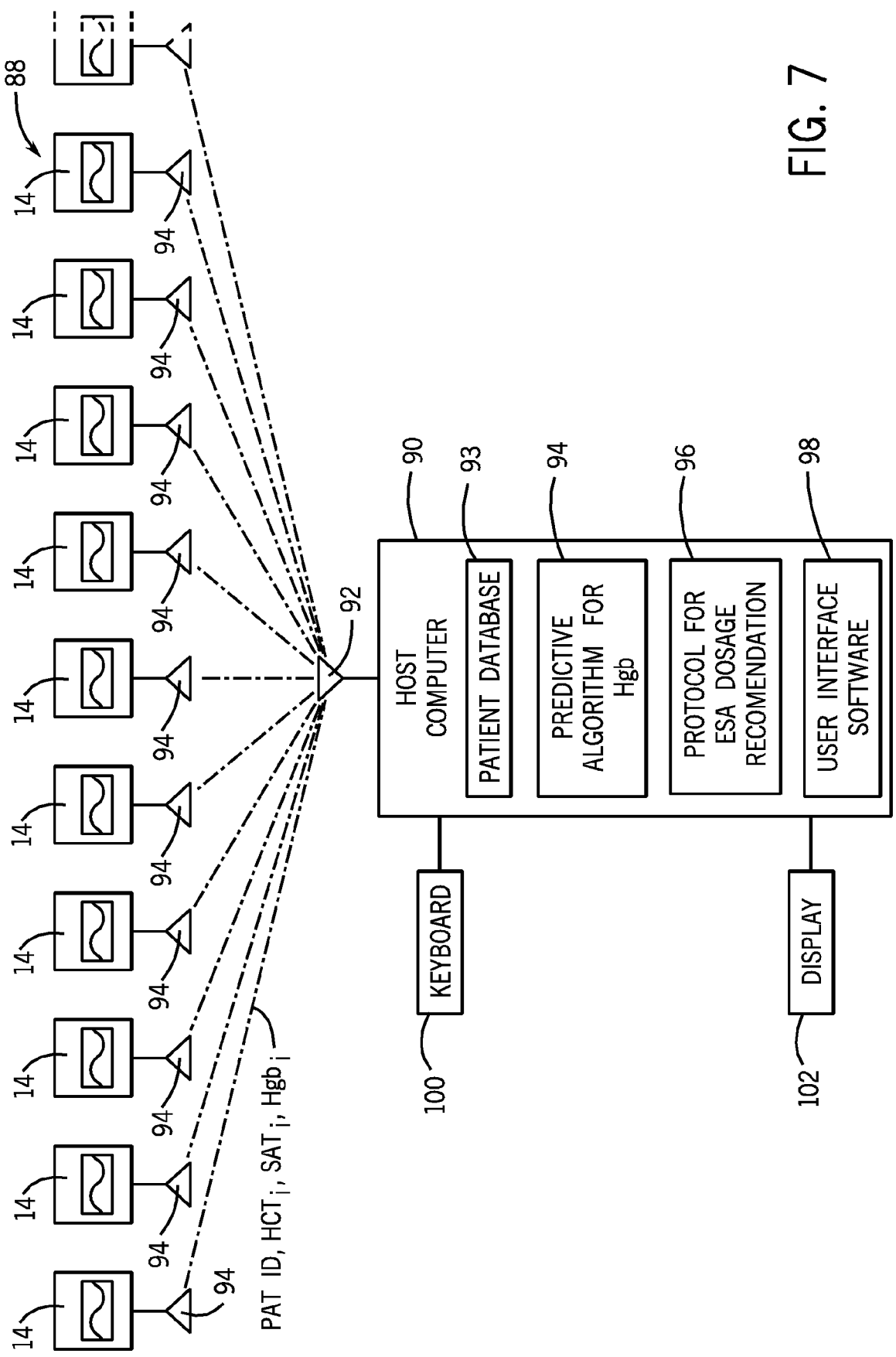
FIG. 7 is a schematic drawing illustrating a hemodialysis patient data acquisition and management system operating in accordance with a preferred embodiment of the invention and being implemented in a hemodialysis center having a plurality of hemodialysis systems for which a non-invasive optical blood monitor is used to monitor the blood of the patient during the treatment session.

FIG. 7 illustrates a wireless example of a hemodialysis patient data acquisition, management and analysis systems 88 implemented in accordance with a preferred embodiment of the invention. In FIG. 7, a host computer 90 has a wireless communication device 92 that communicates with a wireless communication device 94 associated with each of several optical blood monitors 14 located within a hemodialysis clinic. While FIG. 7 illustrates a wireless communication network, the invention could of course be implemented using another type of network. As mentioned, the optical blood monitor 14 stores in memory the session commencement data, Pat. ID, $HCT_i$, $SAT_i$ $Hgb_i$, and time and date stamp for each respective patient taken at the onset of each respective hemodialysis treatment session. This data (Pat. ID, $HCT_i$, $SAT_i$ $Hgb_i$, and time and date stamp) is downloaded via the wireless network from the optical blood monitor 14 to the host computer 90 and entered into a patient database 93 on the host computer.

In accordance with the invention, the host computer 90 contains software which implements a patient database 93, the predictive algorithm for hemoglobin 94, protocol for ESA dosage recommendations 96, and user interface software 98. A keyboard 100 and display 102 are also provided with the host computer 90, as is well known. While the display 68 on the respective optical monitors 14 are each located near the patient 10, the host computer 90 is located in a central location and is not specific to any particular patient or hemodialysis station.

The patient database 93 preferably contains session commencement data for each of the patients that are treated at the hemodialysis center. The patient database 93 can be programmed using any suitable database package, such as Microsoft Access™. The software modules for the predictive algorithm, the ESA protocol and user interface screens are custom programmed. The user interface software 98 on the host computer enables an attending physician or nurse to observe and analyze the patient's trends in hemoglobin, or hematocrit and oxygen saturation values over the long-term. The data in the patient database 93 is also used as input to the predictive algorithm for estimating the patient's hemoglobin level at his her next visit, see block 94. The result of the predictive algorithm 94 is then used in connection with historical records of the patient's session commencement data, by software, block 96, and implementing protocol for ESA dosage recommendations, as will be described in more detail below.

Figure 8:
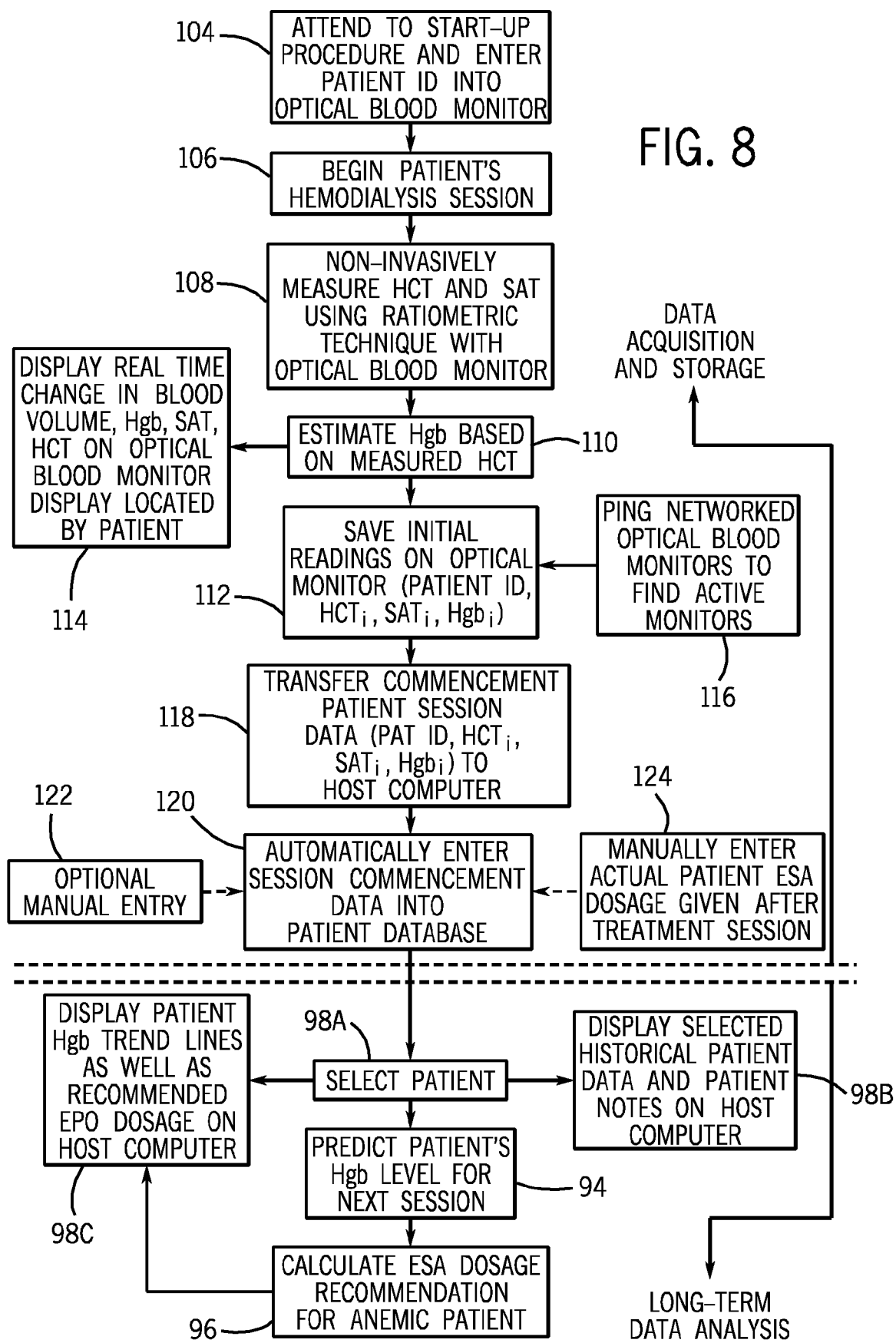
FIG. 8 is a block diagram illustrating the operation of the preferred embodiment of the invention.

FIG. 8 is a flow diagram illustrating the operations of various aspects of the invention in more detail. Referring to block 104, when the patient arrives at the clinic, the clinician attends to the appropriate hemodialysis startup procedures, and enters the patient ID number into the optical blood monitor 14 associated with the respective hemodialysis system, as described above. Once the startup procedure is complete, the patient's hemodialysis session begins, block 106. As soon as the patient's blood is believed to be stable, the user starts the blood monitor 14 to non-invasively measure the patient's hematocrit and oxygen saturation levels using ratiometric techniques, as explained in the above incorporated, co-pending patent application. Once the hematocrit and oxygen saturation values are measured and calculated in the optical blood monitor, see block 108, the controller 35 for the optical blood monitor estimates the hemoglobin level based on the measured hematocrit level, see block 110. The preferred method for estimating hemoglobin based on the measured hematocrit level is disclosed in the above-noted incorporated patent application. Block 112 shows that the initial readings on the optical blood monitor taken at the onset of the patient's hemodialysis treatment session, namely the patient ID, $HCT_i$, $SAT_i$ $Hgb_i$, and a time and date stamp are saved in memory on the optical monitor 14. In addition, as described in block 114, real-time data representing the change in blood volume, hematocrit, hemoglobin and oxygen saturation levels are displayed on the display 68 for the optical blood monitor 14 in accordance with the prior art.

Referring now to blocks 116 and 118 in FIG. 8, the preferred controller 35 for the optical blood monitors 14 includes a commercially available interface for passing data from the controller 35 to a host computer. In the preferred embodiment of the invention, this interface is custom configured to store the session commencement data (patient ID, $HCT_i$, $SAT_i$ $Hgb_i$, and time and date stamp) at the beginning of the patient's hemodialysis session. The preferred patient data collection system inside the controller 35 uses a circular or "round robin" buffer, which is continually reloaded with the latest sample data as well as monitor status and the treatment commencement data information of interest. When data is requested, the controller 35 for the optical blood monitor 14 downloads the next message in the queue. Preferably, the controller 35 for the optical blood monitor interfaces by serial hub with the host computer 90, although the use of a network adapter or variety of other radio-linking equipment should be suitable. For example, a wireless radio link from Aerocom operating at 2.4 GHz is suitable. Each radio 94 connected to an optical blood monitor 14 is configured at the factory to operate as an end user, and the radio 92 for the host computer is designated as a hub radio. One suitable method of modulation for the radio system is a spread spectrum method in which the bit patterns change by a pseudo random algorithm or where the frequency of the radio system varies based on a similar pseudo random basis. The use of such a spread spectrum technique allows for multiple radios 94 to operate using the same modulation category on the same frequency without interference.

Once the wireless radio system is set up, the hub radio 92 associated with the host computer 90, passes broadcast messages from the host computer 90 to the end user radios 94. If the host computer 90 calls out a message to a particular blood monitor 14 through the hub radio 92, all end user radios 94 receive that message and pass the message to their associated blood monitor 14. Only the controller 35 for the blood monitor 14 for which the message is intended, i.e. the message includes the appropriate serial number for the respective blood monitor, will respond via its end user radio 94. The host computer 90 preferably includes software that polls or pings the blood monitor network periodically (for example every five minutes) to determine which blood monitors 14 are active, see block 116 in FIG. 8. If a newly identified blood monitor 14 is online, the monitor 14 is prompted to transfer the session commencement data (patient ID, $HCT_i$, $SAT_i$, $Hgb_i$, and time and date stamp) to the host computer 90, see block 118 in FIG. 8. As mentioned, this data is taken in the beginning minutes of the treatment which is the most representative of the patient's true condition, because the body has established equilibrium since the previous treatment, typically two or three days prior. Once ultra filtration of the patient's blood begins, then the body fluids are dynamic and are no longer useful to characterize a patient's steady state fluid or anemia condition.

Referring still to FIG. 8, the patient data transferred to the host computer, block 118, is automatically entered into a patient database 93, see block 120. Blocks 122 and 124 indicate that data may also be entered manually into the patient database 93. Block 122 indicates that optional manual entries may be made, for example, hemoglobin values measured on a monthly basis with standard laboratory blood work. Block 124 indicates that the attending staff manually enters the patient's ESA dosage.

Once the session commencement data is loaded into the patient database 93, it is available to be used for long-term data analysis. The preferred user interface screens are shown in FIGS. 9 through 13. Briefly, the user of the software on the host computer 90 first selects a patient, blocks 98A. Block 98B in FIG. 8 corresponds to the computer interface screen shown in FIG. 11. Block 98C shown in FIG. 8 corresponds to the screen shown in FIG. 10. All of the user interface screens will be discussed in more detail below with respect to FIGS. 9-13. Once the user selects the patient, the software predicts the patient's hemoglobin level for the next session, block 94, using the regression model discussed earlier. The preferred system also calculates an ESA dosage recommendation for anemic patients, block 96. The preferred ESA protocol is put forth below in Tables 2A and 2B.

TABLE 2A

| HD: ESA Protocol | |
| --- | --- |
| Rising Hemoglobin | Falling Hemoglobin or Constant Hemoglobin |
| Observed Hgb <10 g/dl | Observed Hgb <10 g/dl |
|   If Predicted or Observed (P/O) Hgb rising by <0.4 g/dl/2 wks: |   Increase ESA dose 50% |
|     Increase ESA dose by 25% | |
|   If P/O Hgb rising by 0.4-0.7 g/dl/2 wks: | |
|     No dose change | |
|   If P/O Hgb rising by >0.7 g/dl/2 wks: | |
|     Decrease ESA dose by 10% | |
|     Observed Hgb <11 g/dl |     Observed Hgb 10.0-10.9 g/dl |
|   If Predicted/Observed Hgb rising by <0.4 g/dl/2 wks: |   If Predicted/Observed Hgb decreasing >0.7% g/dl/2 wks: |
|     Increase ESA dose 25% |     Increase ESA dose 50% |
|   If P/O Hgb rising by 0.4-0.7 g/dl/2 wks: |   If P/O Hgb decreasing 0.4-0.7 g/dl/2 wks: |
|     No dose change |     Increase ESA dose 25% |
|   If P/O Hgb rising by >0.7 g/dl/2 wks: |   If P/O Hgb decreasing <0.4 g/dl/2 wks: |
|     Decrease ESA dose 10% |     Increase ESA dose by 15% |
|     Observed Hgb <11-12 g/dl |     Observed Hgb 11-12 g/dl |
|   If Predicted/Observed Hgb rising by >0.7 g/dl/2 wks. |   If Predicted/Observed Hgb decreasing <0.4 g/dl/2 wks. |
|     Decrease ESA dose 50% |     No dose change |
|   If P/O Hgb rising 0.4-0.-0.7 g/dl/2 wks: |   If P/O Hgb decreasing by 0.4-0.7 g/dl/2 wks: |
|     Decrease ESA dose 25% |     Increase ESA dose 25% |
|   If P/O Hgb rising <0.4 g/dl/2 wks: |   If P/O Hgb decreasing by >0.7 g/dl/2 wks: |
|     No dose change |     Increase ESA dose 50% |
|     Observed Hgb <12.1-13 g/dl |     Observed Hgb >12 g/dl |
|   If Predicted/Observed Hgb rising by >0.7 g/dl/2 wks. |   If Predicted/Observed Hgb decreasing <0.4 g/dl/2 wks. |
|     Decrease ESA dose 50% |     Decrease ESA dose by 15% |
|   If P/O Hgb rising 0.4-0.7 g/dl/2 wks: |   If P/O Hgb decreasing by 0.4 g/dl/2 wks: |
|     Decrease ESA dose 25% |     No dose change |
|   If P/O Hgb rising <0.4 g/dl/2 wks: |   If P/O Hgb decreasing by >0.4-0.7 g/dl/2 wks: |
|     Decrease ESA dose 15% |     Increase ESA dose 25% |
| |   If P/O Hgb decreasing by >0.7 g/dl/2 wks: |
| |     Increase ESA dose 50% |

TABLE 2A-continued

HD: ESA Protocol

| Rising Hemoglobin | Falling Hemoglobin or Constant Hemoglobin |
|---|---|
| Observed Hgb <13.1-14 g/dl<br>If Predicted/Observed Hgb rising by >0.4 g/dl/ 2 wks.<br>  Decrease ESA dose 50%<br>If P/O Hgb rising by <0.4 g/dl/2 wks:<br>  Decrease ESA dose 25%<br>If Observed Hgb >13 g/dl for 3 consecutive months:<br>  Hold ESA dose | Observed Hgb >13.1-14 g/dl<br>Decrease ESA by 25% then<br>  If Predicted/Observed Hgb decrease by <0.4 g/dl/ 2 wks.<br>    Decrease ESA dose by another 15%<br>  If P/O Hgb decreases by 0.4 g/dl/2 wks:<br>    No further ESA dose change<br>  If P/O Hgb decreases by >0.4-0.7 g/dl/2 wks:<br>    Increase ESA dose by 15%<br>  If P/O Hgb decrease by >0.7 g/dl/2 wks:<br>    Increase ESA dose by 25% |
| Observed Hgb >14 g/dl<br>Hold ESA dose, then<br>  When Observed Hgb <13 g/dl<br>    Restart ESA at 50% dose reduction | Observed Hgb >14 g/dl<br>Hold ESA dose, then<br>  When P/O Hgb <13 g/dl<br>    Restart ESA at 50% dose reduction |

TABLE 2B

Constant Hemoglobin

Observed Hgb <10 g/dl
  Increase ESA dose 50%
Observed Hgb 10.0-10.9 g/dl
  Increase ESA dose 25%
Observed Hgb 11-12 g/dl
  No dose change
Observed Hgb 12.1-13 g/dl
  Decrease ESA dose by 25%
Observed Hgb 13.1-14 g/dl
  Decrease ESA by 25%, then
  If Predicted Hgb decrease by <0.4 g/dl/2 wks.
    Decrease ESA dose by another 15%
  If Predicted Hgb decreases by 0.4-0.7 g/dl/2 wks.
    No further ESA dose change
  If Predicted Hgb decreases by >0.7 g/dl/2 wks.
    Increase ESA dose by 15%
Observed Hgb >14 g/dl
  Hold ESA dose, the
When Observed Hgb <13 g/dl
  Restart ESA at 50% dose reduction In Tables 2A and 2B, the preferred protocol bases the percentage change in ESA dosage from the previous treatment session on several factors, including the observed patient hemoglobin level taken at the onset of the current hemodialysis treatment session (i.e., observed Hgb), as well as two-week trending of the predicted and observed hemoglobin level (i.e. P/O, gm/dl/2 wks). More specifically, the preferred protocol subtracts the mean of the three second-most recently observed Hgb levels for the patient from the mean of the three most recently observed Hgb levels to determine an observed two-week ΔHgb. The preferred protocol also subtracts the mean of the three second-most recently predicted Hgb levels for the patient from the mean of the three most recently predicted Hgb levels to determine a predicted two-week ΔHgb. The values (P/O) in Table 2A is the minimum (in terms of magnitude) of the observed two-week ΔHgb and the predicted two-week ΔHgb. The Rising Hemoglobin column in Table 2A is selected if the P/O is a positive value, and the Falling Hemoglobin column is selected if the P/O is a negative value. The Constant Hemoglobin Table 2B is chosen if P/O is equal to zero within one significant figure. The preferred protocol and the use of two-week trending are desirable in order to lessen short term data effects on recommended dosing. In general, it is desirable to maintain each patient's Hgb levels over the long term within a narrow preferred range, e.g., Hgb between 11-12 gm/dl, while at the same time maintaining the patient's ESA dosage at an appropriate and relatively constant level over the long term.

Preferably, the protocol outputs a recommended ESA dosage based on the rules in the tables above. However, in the preferred embodiment of the invention, if the observed or predicted hemoglobin level drops below a predetermined level (for example 7 gm/dl) or if the observed or predicted hemoglobin level rises above a predetermined value (for example 17 gm/dl), the system sets an alarm or an alert to seek medical help. Also, while the above ESA protocol does not account for the effects of intravenous iron therapy, such therapy typically increases the hemoglobin level and therefore a decrease in the ESA dosage of 25% beyond what is called for by the protocol in the above table is likely appropriate.

Those skilled in the art will recognize that modifications can be made to the ESA protocol without departing from the spirit of the invention. For example, the protocol can be modified to compare data trends for shorter or longer time periods than two weeks, or it can be modified to be based solely on observed values, solely on predicted values or on a different combination of observed and predicted values than are presented specifically in Tables 2A and 2B. Further, amount of the percentage ESA dosage change can be modified depending, for example, on the specific medication.

Once a patient has ended his or her treatment session, the attending staff prescribes an ESA dosage which is administered to the patient. At that point, the staff should enter the actual ESA dosage manually into the patient database, box 124 in FIG. 8. The patient is then weighed and released, and the database 93 is loaded with data for the next treatment session for the patient.

Referring now to FIG. 9, the Patient List screen 98A includes a listing of patient identification numbers 126. A patient identification number 126 is set up for each hemodialysis patient that is serviced by the clinic. If desirable and appropriate, each patient ID is associated with a patient's name, see drop-down box 127, although as mentioned before, care must be taken to respect patient privacy laws. For example, it may be necessary to provide accessibility to the database software only by user name and password in order to protect the patient's privacy. For each patient in the database, the Patient List screen 125 lists a desired minimum hemoglobin level and a desired maximum hemoglobin level which had been entered into the system by the clinician, nurse or physician. The Patient List screen 125 also lists observed hemoglobin levels for the patient (i.e. optically observed $Hgb_i$), and in particular, the minimum value for that patient in the database, the maximum value for that patient in the database, and the patient's last observed $Hgb_i$ value. Further, the Patient List screen lists the last ESA dose for the patient, as well as the calculated ESA dose for the current treatment session. Once a patient has been released, the calculated ESA dosage listed in the Patient List screen 125 does not change until the patient's next treatment session. The "Order by Name" button 129 rearranges the list by patient name, rather than patient identification number. The "Get Data" button 131 allows the user to manually prompt the system so that the host computer interrogates the network of optical blood monitors to download additional data. In order to view additional data for any given patient, the user selects a patient number on screen 125 and then selects one of tab 130 for a "Patient Management" screen (FIG. 10) or tab 132 for a "Patient Graph" screen. Tab 134 redirects the user to an "Active Patients" screen (FIG. 12) and tab 136 directs the user to an "Outside Boundaries" screen (FIG. 13).

Figure 10:
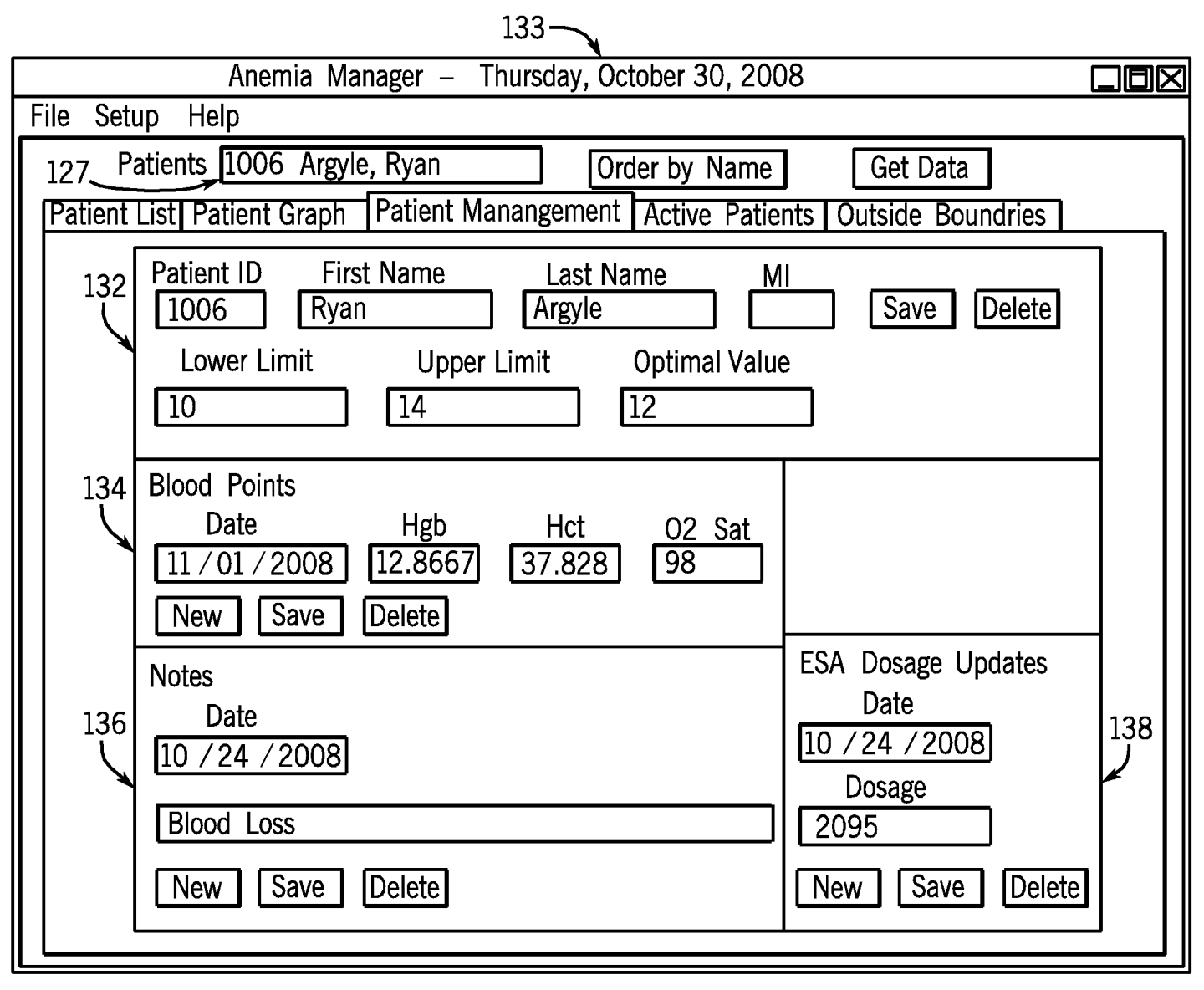

The Patient Management screen 133 is shown in FIG. 10. Window 132 provides prompts for adding new patient information or editing patient information. The fields in window 132 are patient ID, patient Name, Lower limit which is the desired minimum hemoglobin value for the patient, Upper limit which is the desired maximum hemoglobin level for the patient, and Optimal Value which is the desired hemoglobin level for the patient. These values, as mentioned before, are entered by staff. When the values in window 132 or the patient identification number are changed, the user selects the "Save" button in window 132 to add the new patient or edit the values for an existing patient. The "Delete" button is used to remove the patient from the database.

The "Blood Points" window 134 lists session commencement data stored in the patient database on the date selected. The prompt label date includes a dropdown listing of all the dates in which blood data has been entered for the patient, normally automatically (see, box 120 in FIG. 8). However, data for any particular date can be entered manually as well, see box 122 in FIG. 8. The "Save" button in the "Blood Points" window 134 is used to edit the values for Hgb, HCT and oxygen saturation for a particular date. The "New" button is used to add blood data for a new date. The "Delete" button in the "Blood Points" window 134 can be used to remove data for the identified patient on the particular listed date.

The Patient Management screen 133 also preferably includes a "Notes" window 136 in which staff can enter and store notes on a particular date for a particular patient. The Patient Management screen 133 also includes an "ESA Dosage" window 138 in which staff manually enters, edits or deletes a dosage that has been administered to the patient on a given date. All of the information entered in the Patient Management screen 133 is stored in the patient database 93. The user of the software can access the data for a given patient in windows 134, 136 and 138 on various dates by merely selecting a different date under the date prompt. The user can change the identified patient using the patient ID prompt in window 132.

Figure 11:
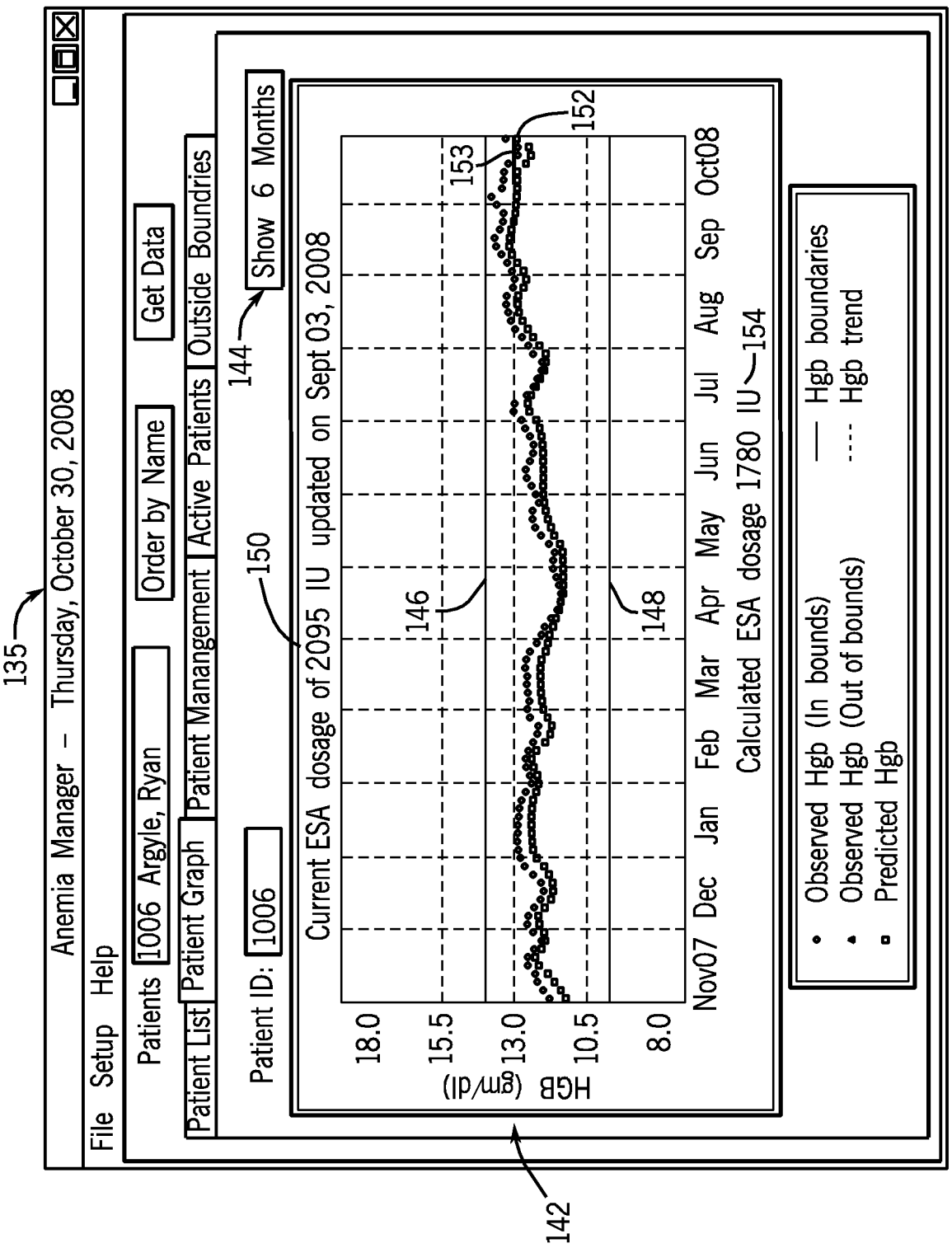

Turning now to the Patient Graph screen in FIG. 11, the Patient Graph screen 135 includes a graph 142 which displays a trend of the patient's (patient ID #1006) hemoglobin levels, both measured (open circles) and predicted (open squares). The graph 142 preferably includes horizontal lines 146 and 148 which correspond to the maximum desired hemoglobin level (146) and the minimum desired hemoglobin level (148) for the patient. It can be seen on the graph 142 in FIG. 11 that the patient's measured hemoglobin levels, as well as the predicted hemoglobin levels, are trending slightly upward, yet still between the maximum desired level 146 and the minimum desired level 148.

Above the graph 142, the software lists the current ESA dosage for the patient 150 (meaning the last dosage prescribed). The predicted hemoglobin level for the patient's next visit is plotted on the graph 142, see reference number 152. The Patient Graph display screen 135 also indicates the calculated ESA dose for the patient (per the ESA protocol) at the end of the current treatment session, see reference number 154. The graph 142 in FIG. 11 also shows a trend line 153 which is a linear regression through the last six data points. Other information can be displayed on the Patient Graph screen 135, as desired. For example, it may be desirable to display the predicted hemoglobin value numerically on the screen 135, or it may be desired to provide an alert in case the trend line 153 is too steep, or the predicted or observed hemoglobin values fall beyond the desired minimum and maximum levels 148 and 146, respectively. The software also preferably provides a "Show 6 Months" button 144 which adjusts the time scale in the graph 142 at a six month time period.

As can be seen in FIG. 11, use of the system allows the attending staff to easily analyze the long-term trend of the patient and facilitate informed decision making. Use of the system promotes more frequent hemoglobin monitoring for each individual patient, which in turn should reduce undesirable fluctuations in patient hemoglobin levels. Frequent hemoglobin monitoring allows early detection of trends in the hemoglobin slope lines, and also early evidence of the patient's response to ESA dosages and perhaps alert the staff that more appropriate anemia management tools may be needed.

The "Active Patients" screen 137 is shown in FIG. 12. Screen 137 lists each of the active optical monitors 14 in the main window 154. The first column labeled "SID" lists the Station ID, for example hemodialysis station #11 or #14, as shown in FIG. 12. The second column lists the patient ID number for the active stations as well as the same information that was listed for that patient in the Patient List screen 125 shown in FIG. 9.

The "Outside Boundaries" screen 139 is shown in FIG. 13. The purpose of this screen is to list all patients whose initial hemoglobin readings ($Hgb_i$) are out of bounds. The data listed for each patient is again similar to that shown in the Patient List screen 125, however, in the Outside Boundaries screen 139, only patients whose hemoglobin level is currently out of bounds are listed.

The described embodiment of the invention should be considered in all respects as illustrative and not restrictive. For example, as mentioned above, the preferred means for communicating data between the controller for the blood monitor and the host computer is a wireless communication device, although other means of data communication may be used. In addition, various aspects of the system can be implemented without implementing other aspects of the system. For example, the system can be implemented with the predictive algorithm for the hemoglobin without implementing the protocol for ESA dosage recommendations. Also, the system can be implemented with the patient database and the user software interface screens without using either the predictive algorithm for the hemoglobin level or the software for the ESA protocol dosage recommendations. Even in such a system, the patient management 133, patient graph 135 and outside boundaries 137 screens can be quite useful to attending staff for following trends of a patient's hemoglobin levels. On the other hand, it would be quite possible to implement the predictive hemoglobin algorithm and/or the protocol for the ESA dosage recommendations, in environments other than one in which optically monitored hemoglobin levels are downloaded automatically from the optical blood monitors to the host computer. For example, the data could be entered in a manual form into a patient database.

We claim:

1. An anemia management system for hemodialysis patients comprising:
    at least one hemodialysis system for drawing blood from a patient, passing the drawn blood through extracorporeal tubing and through a dialyzer, and returning the dialyzed blood through extracorporeal tubing to the patient, the hemodialysis system comprising:
        a blood chamber having an inlet and an outlet which are connected in line with the extracorporeal tubing of the hemodialysis system and a fluid passageway through which the drawn blood flows;
        a first photo emitter for emitting light at a first wavelength through the blood chamber and the drawn blood flowing through the blood chamber;
        a second photo emitter for emitting light at a second wavelength through the blood chamber and the drawn blood flowing through the blood chamber; and
        at least one photo detector for detecting the intensity of light at the first and second wavelength after it passes through the blood chamber and the drawn blood flowing through the blood chamber;
    a computing system, connected to the at least one hemodialysis system, the computing system comprising processor-executable instructions, stored on one or more non-transitory processor-readable media, and one or more processors for executing the processor-executable instructions, wherein the processor-executable instructions include instructions for:
        receiving a signal representing the detected light intensity levels from the at least one hemodialysis system;
        determining a value representing the patient's hemoglobin level based on the received signal;
        storing the determined value in a patient database of the computing system;
        determining, based on information stored in the patient database, a predicted value for the patient's hemoglobin level at the onset of a next treatment session by applying a statistical model to stored patient data, where the predicted value is based on multiple instances of the patient's previous hemoglobin levels corresponding to measurements taken at the onset of a series of treatment sessions, multiple coefficients determined based on the statistical model with each coefficient corresponding to one of the multiple instances of the patient's previous hemoglobin levels, and at least one previously administered dosage of an erythropoiesis stimulating agent (ESA);
        determining a recommended ESA dosage for the patient based on the predicted value; and
        outputting the recommended ESA dosage via an output interface of the computing system.

2. The anemia management system as recited in claim 1, wherein the first photo emitter emits light at a wavelength of substantially 800 nm, and the second photo emitter emits light at a wavelength of substantially 1300 nm.

3. The anemia management system as recited in claim 1, wherein the computing system is further configured to determine a hematocrit value and an oxygen saturation value for the patient, as well as time and date information at the onset of the patient's hemoglobin treatment session.

4. The anemia management system as recited in claim 3, wherein the at least the first and second photo emitters of the non-invasive blood monitor emit light at a wavelength of substantially 800 nm and substantially 1300 nm, respectively, and a third photo emitter emits light at a wavelength of substantially 660 nm.

5. The anemia management system as recited in claim 1, wherein determining the statistical model is a cross-sectional regression model based on statistical analysis of data collected from a plurality of hemodialysis patients over a number of hemodialysis treatment sessions being monitored by a non-invasive blood monitor.

6. The anemia management system as recited in claim 1, wherein determining the predicted value is based on the following equation:

$$\text{Predicted Hgb Value} = A*(\text{Hgb of Last Period}) + B*(\text{Hgb of Second to Last Period}) + C*(\text{Hgb of Third to Last Period}) + D*(\text{Last ESA Dose value}) + E$$

where Hgb of last period, Hgb of second to last period and Hgb of the third to last period represent the patients hemoglobin levels monitored at the previous three hemodialysis treatment sessions, the last ESA dose value represents the ESA dose administered to the patient at the patient's last treatment session, the values A through E are statistical regression coefficients, and the predicted Hgb value represents the predicted value of the patient's hemoglobin level at the start of the next treatment session.

7. The anemia management system as recited in claim 6, wherein the ESA is recombinant erythropoietin, and the regression coefficient A is substantially equal to 0.4784356, the regression coefficient B is substantially equal to 0.2042212, the regression coefficient C is substantially equal to 0.222685, the regression coefficient D is substantially equal to 0.0000396, and the regression coefficient E is substantially equal to 0.9627966.

* * * * *